United States Patent
Pepper et al.

(10) Patent No.: US 11,660,133 B2
(45) Date of Patent: May 30, 2023

(54) BONE COUPLING DEVICE AND METHOD

(71) Applicant: Zimmer, Inc., Warsaw, IN (US)

(72) Inventors: John R. Pepper, New Haven, CT (US); Lon S. Weiner, Rumson, NJ (US); Stuart D. Katchis, Scarsdale, NY (US); Gregory J. Denham, Warsaw, IN (US); Thomas Holton, Warsaw, IN (US); Ryan D. Schlotterback, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 142 days.

(21) Appl. No.: 16/666,014

(22) Filed: Oct. 28, 2019

(65) Prior Publication Data

US 2020/0129214 A1    Apr. 30, 2020

Related U.S. Application Data

(60) Provisional application No. 62/751,168, filed on Oct. 26, 2018.

(51) Int. Cl.
    *A61B 17/86*    (2006.01)
    *A61B 17/72*    (2006.01)
    (Continued)

(52) U.S. Cl.
    CPC ........ *A61B 17/8685* (2013.01); *A61B 17/864* (2013.01); *A61B 17/8625* (2013.01);
    (Continued)

(58) Field of Classification Search
    CPC . A61B 17/7291; A61B 17/8685; A61C 8/006; A61C 8/0062
    See application file for complete search history.

(56) References Cited

U.S. PATENT DOCUMENTS

| 3,991,425 A | 11/1976 | Martin et al. |
| 4,246,662 A | 1/1981 | Pastrick |
| (Continued) | | |

FOREIGN PATENT DOCUMENTS

| AU | 2019366821 A1 | 4/2021 |
| DE | 19949890 A1 | 6/2001 |
| (Continued) | | |

OTHER PUBLICATIONS

International Search Report and Written Opinion dated Jan. 31, 2020.

(Continued)

*Primary Examiner* — Samuel S Hanna
(74) *Attorney, Agent, or Firm* — Schwegman Lundberg & Woessner, P.A.

(57) ABSTRACT

A bone coupling device is configured for joining a first bone piece to a second bone piece which includes a first component having an inner surface bounding a first cavity and a first stem portion for insertion into the first bone piece. A second component includes a second stem portion for insertion into the second bone piece and an axially extending connector extending from the second stem portion and configured to be inserted into the first cavity. The connector has an outer surface which is complementarily shaped relative to an inner surface to inhibit rotation relative to each other when the connector is received in the cavity to engage the first component and the second component.

9 Claims, 29 Drawing Sheets

(51) Int. Cl.
 *A61B 17/56* (2006.01)
 *A61B 17/00* (2006.01)
(52) U.S. Cl.
 CPC .............. *A61B 2017/00482* (2013.01); *A61B 2017/564* (2013.01)

(56) References Cited

U.S. PATENT DOCUMENTS

| | | |
|---|---|---|
| 4,304,011 A | 12/1981 | Whelan, III |
| D277,784 S | 2/1985 | Sgarlato et al. |
| 4,908,031 A | 3/1990 | Frisch |
| 5,037,440 A | 8/1991 | Koenig |
| 5,047,059 A | 9/1991 | Saffar |
| 5,062,851 A | 11/1991 | Branemark |
| 5,167,661 A | 12/1992 | Wagenknecht |
| 5,207,712 A | 5/1993 | Cohen |
| 5,219,903 A | 6/1993 | Fujii et al. |
| 5,290,314 A | 3/1994 | Koch et al. |
| 5,417,692 A | 5/1995 | Goble et al. |
| 5,443,467 A | 8/1995 | Biedermann et al. |
| 5,643,267 A | 7/1997 | Hitomi et al. |
| 5,683,466 A | 11/1997 | Vitale |
| 5,725,581 A | 3/1998 | Branemark |
| 5,810,591 A | 9/1998 | Huber |
| 5,810,822 A | 9/1998 | Mortier |
| 5,827,285 A | 10/1998 | Bramlet |
| 5,919,193 A | 7/1999 | Slavitt |
| 6,001,103 A | 12/1999 | Hitomi et al. |
| 6,099,571 A | 8/2000 | Knapp |
| 6,284,001 B1 | 9/2001 | Knapp |
| 6,383,223 B1 | 5/2002 | Baehler et al. |
| 6,413,260 B1 | 7/2002 | Berrevoets et al. |
| 6,454,808 B1 | 9/2002 | Masada |
| 6,458,134 B1 | 10/2002 | Songer et al. |
| 6,517,543 B1 | 2/2003 | Berrevoets et al. |
| 6,602,293 B1 | 8/2003 | Biermann et al. |
| 6,852,113 B2 | 2/2005 | Nathanson et al. |
| 6,964,994 B1 | 11/2005 | Antonietti et al. |
| 7,041,106 B1 | 5/2006 | Carver et al. |
| 7,214,226 B2 | 5/2007 | Alleyne |
| 7,291,175 B1 | 11/2007 | Gordon |
| 7,297,165 B1 | 11/2007 | Kriek |
| 7,611,526 B2 | 11/2009 | Carl et al. |
| 7,635,364 B2 | 12/2009 | Barrall et al. |
| 7,837,738 B2 | 11/2010 | Reigstad et al. |
| 7,951,198 B2 | 5/2011 | Sucec et al. |
| 8,100,983 B2 | 1/2012 | Schulte |
| 8,303,589 B2 | 11/2012 | Tyber |
| 8,313,487 B2 | 11/2012 | Tyber |
| 8,328,806 B2 | 12/2012 | Tyber |
| 8,617,227 B2 | 12/2013 | Sucec et al. |
| 8,715,325 B2 | 5/2014 | Weiner et al. |
| 8,764,842 B2 | 7/2014 | Graham |
| 8,945,232 B2 | 2/2015 | Sander et al. |
| 9,011,504 B2 | 4/2015 | Reed |
| 9,072,562 B2 | 7/2015 | Weiner et al. |
| D749,738 S | 2/2016 | Weiner et al. |
| 9,271,775 B2 | 3/2016 | Lavi |
| 9,468,465 B2 | 10/2016 | Weiner et al. |
| 9,504,582 B2 | 11/2016 | Sander et al. |
| 9,615,873 B2 | 4/2017 | Weiner et al. |
| 9,687,286 B2 | 6/2017 | Weiner et al. |
| 10,085,779 B2 | 10/2018 | Hoogervorst |
| 10,278,828 B2 | 5/2019 | Sander et al. |
| 10,357,299 B2 | 7/2019 | Weiner et al. |
| 10,383,669 B2 | 8/2019 | Graham |
| 2004/0127900 A1 | 7/2004 | Konieczynski et al. |
| 2004/0220678 A1 | 11/2004 | Chow et al. |
| 2005/0043732 A1 | 2/2005 | Dalton |
| 2005/0113830 A1 | 5/2005 | Rezach et al. |
| 2005/0192587 A1 | 9/2005 | Lim |
| 2006/0052878 A1 | 3/2006 | Schmieding |
| 2006/0074492 A1 | 4/2006 | Frey |
| 2006/0195087 A1 | 8/2006 | Sacher et al. |
| 2008/0065224 A1 | 3/2008 | Reigstad et al. |
| 2008/0097611 A1 | 4/2008 | Mastrorio et al. |
| 2008/0045963 A1 | 8/2008 | Abdou |
| 2009/0157121 A1 | 6/2009 | Harris et al. |
| 2010/0036439 A1 | 2/2010 | Waggle |
| 2010/0121325 A1 | 5/2010 | Tyber |
| 2010/0256638 A1 | 10/2010 | Tyber |
| 2011/0004255 A1* | 1/2011 | Weiner .................. A61B 17/68 606/86 R |
| 2011/0054545 A1 | 3/2011 | Champagne |
| 2011/0082508 A1 | 4/2011 | Reed |
| 2011/0118739 A1 | 5/2011 | Tyber |
| 2011/0125153 A1 | 5/2011 | Tyber |
| 2012/0065692 A1 | 3/2012 | Champagne et al. |
| 2013/0123862 A1 | 5/2013 | Anderson et al. |
| 2013/0325138 A1 | 12/2013 | Graham |
| 2014/0107712 A1 | 4/2014 | Fallin et al. |
| 2014/0114365 A1 | 4/2014 | Sucec et al. |
| 2015/0223850 A1 | 8/2015 | Reed |
| 2016/0228163 A1* | 8/2016 | Hulliger ............ A61B 17/8625 |
| 2017/0035472 A1 | 2/2017 | Weiner et al. |
| 2017/0065424 A1 | 3/2017 | Lauf et al. |
| 2017/0290614 A1 | 10/2017 | Weiner et al. |
| 2018/0228522 A1 | 8/2018 | Reed |
| 2018/0303615 A1 | 10/2018 | Papaloizos |
| 2018/0317989 A1 | 11/2018 | Sellers |
| 2019/0059960 A1 | 2/2019 | Shemwell |

FOREIGN PATENT DOCUMENTS

| | | |
|---|---|---|
| DE | 112019005322 T5 | 1/2022 |
| EP | 0524874 A1 | 1/1993 |
| EP | 0831757 B1 | 11/2001 |
| GB | 1582974 A | 1/1981 |
| GB | 2126097 A | 3/1984 |
| GB | 2592160 A | 8/2021 |
| JP | 2005073740 A | 3/2005 |
| WO | WO-9309728 A1 | 5/1993 |
| WO | WO-9605784 A1 | 2/1996 |
| WO | WO-9716137 A1 | 5/1997 |
| WO | WO-0200123 A | 1/2002 |
| WO | WO-2007109752 A2 | 9/2007 |
| WO | WO-2009018527 A1 | 2/2009 |
| WO | WO-2020087086 A1 | 4/2020 |

OTHER PUBLICATIONS

"European Application Serial No. 13186873.9, Extended European Search Report dated Jan. 2, 2014", 6 pgs.
"International Application Serial No. PCT/US2010/024833, International Search Report dated Jul. 9, 2010", 5 pgs.
"International Application Serial No. PCT/US2019/059670, International Preliminary Report on Patentability dated May 6, 2021", 9 pgs.
"United Kingdom Application Serial No. 2106829.1, Examination Report under Section 18(3) dated Jan. 31, 22", 2 pgs.
"BioPro Lower Extremities Products", (2009), 6 pgs.
"Digital Compression Screw Brochure", 16 pgs.
"Digital Compression Screw Brochure No. 17146", Rev. BioPro, Port Huron MI, 2 pgs.
"European Application Serial No. 13187402.0, Extended European Search Report dated May 14, 2014", 1 pg.
"FuturaTM Forefood Implant Arthroplasty Products for the Surgical Treatment of Degenerative Conditions and Deformities Brochure", Nexa Orthopedics, San Diego, CA, Part 1 and Part 2, (2004, 2008), 12 pgs.
"SHIP implant Brochure, Sgarlato Hammertoe Implant Procedure", Sgarlato Labs, Campbell, CA, (2006), 2 pgs.
"Smart ToeTM INtramedullary Shape Memory Implant Brochure", MMI-USA, Memphis, TN, (2009), 2 pgs.
"United Kingdom Application Serial No. 2106829.1, Office Action dated Aug. 19, 2022", 3 pgs.
"Weil-CarverTM Hammertoe Implant Brochure", Biomet Sport Medicine, Warsaw, IN, (2009), 6 pgs.
Caterini, et al., "Arthrodesis of the Toe Joints with an INtramedullary Cannulated Screw for Correction of Hammertoe Deformity", Foot & Ankle International, vol. 25, No. 4., (2004), 256-261.

(56) References Cited

OTHER PUBLICATIONS

Edwards, et al., "Interphalangeal Join Arthrodesis of the Lesser Toes", Foot & Ankle Clinics North America, vol. 7., (2002), 43-48.
Hetherington, "Metatarsalgia and Lesser Metatarsal Surgery", Hallux Valgus and Forefront Surgery textbook, (2000), 429-451.
Iselin, et al.,, "Desarthodesis-Arthroplasties Interphalangiennes Proximales-Conversion to Arthroplasty from Proximal Interphalangeal Joint Arthrodesis", Annales de Chirurgie de la Main, vol. 7, No. 2, (1988), 115-119.
Konkel, et al., "Hammer Toe Correction Using an Absorbable Intrameduallary Pin", Foot & Ankle International, vol. 28, No. 8., (2007), 916-920.
Murray, "Surface Replacement Arthoplasty of the Proximal Interphalangeal Joint", The Journal of Hand Surgery, vol. 32A. no. 6, (2007), 7 pgs.
Sokolow, "une prothese de l'articulation interphlangienne prxirnale osteo-integree: IPP 2. Premier Resultsant13 "Short Term Results of the IPP 2 Proximal Interphalangeal Joint Prosthesisb"", Chirgurgi de la Main , vol. 25, (2006), 280-285.
Stayfuse Tm, "intramedullary Fusion Device for Hammertoe Deformity Brochure", Nexa Orthopedics, San Diego, CA, (Feb. 2010), 8 pgs.

\* cited by examiner

BONE COUPLING DEVICE AND METHOD

CROSS-REFERENCE TO RELATED APPLICATIONS

The present application claims priority to U.S. Provisional Application No. 62/751,168 filed on Oct. 26, 2018, which is incorporated herein by referenced in its entirety.

The present application is related to U.S. Nonprovisional application Ser. No. 13/632,337 filed on Oct. 1, 2010 and issued as U.S. Pat. No. 9,468,465 on Oct. 18, 2016, which application was a continuation-in-part of U.S. Nonprovisional application Ser. No. 12/709,426 filed Feb. 19, 2010, and issued as U.S. Pat. No. 8,715,325 on May 6, 2014 which claimed the benefit of U.S. Provisional Application Ser. No. 61/153,907 filed Feb. 19, 2009, each of which are incorporated herein by reference in their entireties.

TECHNICAL FIELD

This application relates generally to apparatuses, devices, and methods for joining bones and more particularly to bone coupling devices.

BACKGROUND

Hammertoe deformity, the most common deformity of the lesser toes, is a flexion deformity of the proximal interphalangeal (PIP) joint of the toe, with hyperextension of the metatarsophalangeal (MTP) and distal interphalangeal (DIP) joints. Progressive PIP joint flexion deformity typically leads to compensatory hyperextension of the MTP and DIP joints. This makes the PIP joint prominent dorsally. Pain occurs due to rubbing of the prominence against the patient's shoe. The deformity is flexible at first but usually becomes fixed over time. When the deformity is flexible, various procedures can be utilized that involve manipulation of the involved tendons. However, when the deformity is fixed, PIP fusion or joint replacement is often required. Implants available for this purpose include the Weil-Carver™ Hammertoe Implant (Biomet®, Inc., Warsaw, Ind.), Flexible Digital Implant (Tornier, Inc. Edina, Minn.), SHIP Implant (Sgarlato Labs, Campbell Calif.), Digital Compression Screw (BioPro®, Port Huron Mich.), Smart Toe™ Intramedullary Memory Implant (Memometal Inc., Memphis Tenn.), StayFuse™ Intramedullary Fusion Device (Tornier, Inc. Edina, Minn.), and Pro-Toe (Wright Medical, Arlington Tenn.). The latter three implants are used when fusion is desired, since the other implants allow some flexibility of the joint. With all current implants, placement is critical because, when mounted, there is no adjustability following initial implantation in the angle of flexion between the two cut bones to be coupled.

There is thus a need for alternative designs for implants for coupling two bone pieces, including implants that reversibly fix the two bone pieces.

SUMMARY

The present invention provides, in a first aspect, a bone coupling device configured for joining a first bone piece to a second bone piece which includes a first component having an inner surface bounding a first cavity and a first stem portion for insertion into the first bone piece. A second component includes a second stem portion for insertion into the second bone piece and an axially extending connector extending from the second stem portion and configured to be inserted into the first cavity. The connector has an outer surface. The outer surface and the inner surface are complementarily shaped to inhibit rotation relative to each other when the connector is received in the cavity to engage the first component and the second component.

The present invention provides, in a second aspect, a method for use in joining a first bone piece to a second bone piece which includes engaging a first component with the first bone piece by inserting a first stem portion of the first component into the first bone piece. An axially extending connector of a second component is received in a first cavity bounded by an inner surface of the first component. Rotation between the first component and the second component is inhibited by contacting the connector with the inner surface. The connector has an outer surface. The inner surface and the outer surface are complementarily shaped to inhibit rotation relative to each other when the connector is received in the cavity to engage the first component and the second component. The second component is engaged with the first bone piece by inserting a second stem portion of the second component into a second bone piece.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be readily understood from the following detailed description of aspects of the invention taken in conjunction with the accompanying drawings in which:

DETAILED DESCRIPTION

Figure 1:
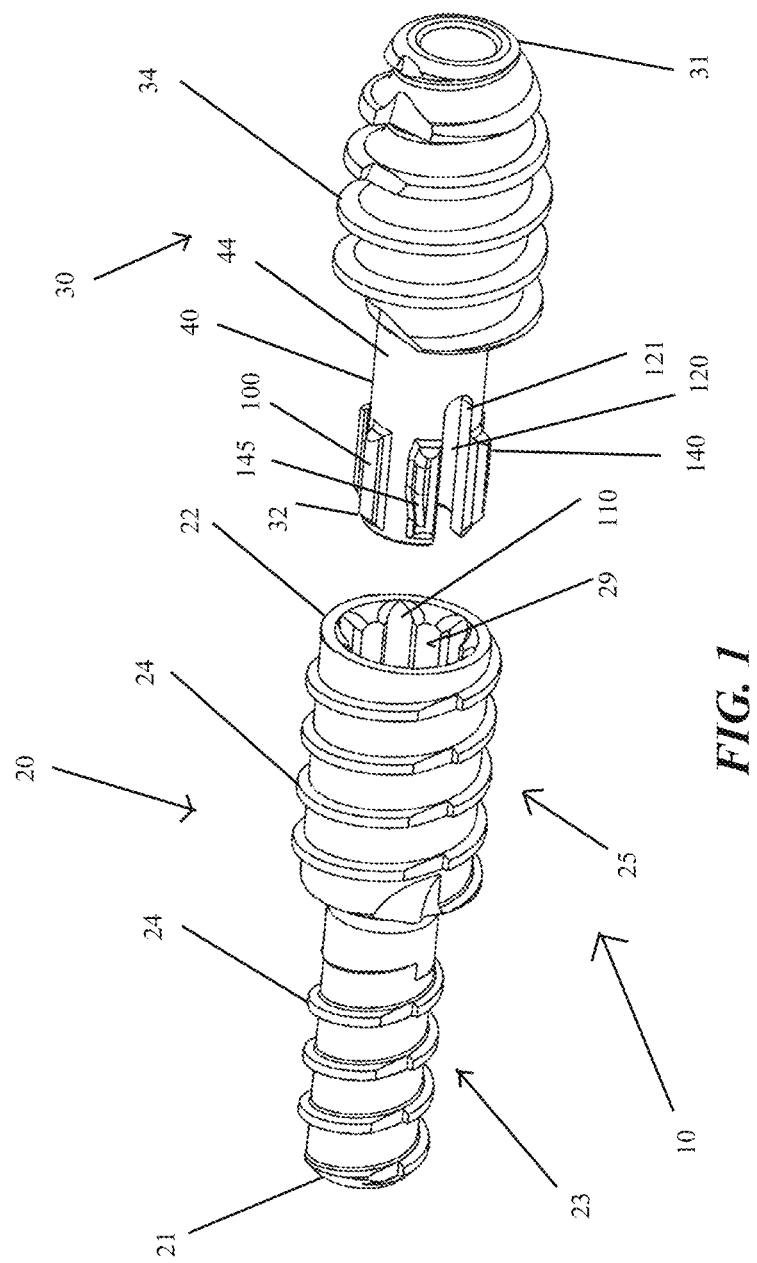
FIG. 1 is a side perspective view of a bone fusion device in accordance with the present invention.

The present disclosure relates to devices and methods for coupling bones with reversibly engaging bone coupling devices. In some embodiments, a reversible bone coupling device facilitates adjustment of an angle between two bones to be coupled, as well as being reversibly engaging to assist in corrections of the coupling of the two bones.

The reversible bone coupling device comprises a first component and a second component. The first component includes a first elongated stem portion comprising a first end and a first top opposite the first end. The first elongated stem portion is suitable for insertion from the first end longitudinally into a surface of a first bone piece of a bone. The second component includes a second elongated stem portion comprising a second end and a second top. The second elongated stem portion is suitable for insertion from the second end longitudinally into a surface of a second bone piece of the bone. The second component further comprises a connector extending from the second top. The connector is capable of coupling with the first component and locking therewith to couple the first component and the second component.

In certain embodiments, the first component is a female component and the second component is a male component. The first elongated stem portion of the female component may comprise an opening that extends axially from the first top toward the first end. The connector may comprise an elongated shaft, a proximal end, a top of shaft near the proximal end, and a distal end, where the connector is capable of insertion into the opening in the first elongated stem portion and locking therein to couple the male component and the female component.

The device is useful for coupling any two bone pieces, and by way of a reversibly engaging mechanism, the connector may be reversed to adjust the position of the connector or remove the connector entirely in situations where adjustment of the device may be necessary or contemplated to further assist in coupling or fusing cut surfaces of bones. As a result, the device is adaptable to any bone size, shape, or configuration of any patient. In some embodiments, the device is particularly useful in coupling or fusing cut surfaces of bones such as cut ends of fingers or toes. This may facilitate the treatment of hammertoe, claw toe, mallet toe, or curly toe. In these embodiments, the first elongated stem portion is suitable for insertion from the first end longitudinally into a cut surface of a resected phalanx, metatarsal or metacarpal, or a cut diaphyhsis, and the second elongated stem portion is suitable for insertion from the second end longitudinally into a cut surface of a resected phalanx, metatarsal or metacarpal, or a cut diaphyhsis.

In the various embodiments described herein and corresponding with the Figures provided herewith, a bone fixation or fusion method and system are described. A first component of a bone fusion device is inserted into a first bone piece. A second component of a bone fusion device is inserted into a second bone piece. A connector of the second component is inserted into a cavity of the first component. The connector is locked within the cavity of the first component by a locking mechanism to facilitate formation of a fused bone. If necessary, the locking mechanism may be adjusted to allow the connector and corresponding second component to be longitudinally adjusted or removed from the first component to facilitate adjustments or modifications during or after surgery.

FIG. 1 illustrates a bone fusion device in accordance with an embodiment of the present disclosure. Bone fusion device 10 includes a female component 20 and a male component 30. Female component 20 is an elongated stem including a first end 21, a first top 22, and a cavity 29. A stem portion 23 extends from first end 21 to a connecting portion 25 which bounds cavity 29. Female component 20 also includes a spiraling thread 24 on the exterior, suitable for screwing female component 20 into a bone or bone piece.

Male component 30 is an elongated stem comprising a second end 31 and a second top 32. Male component 30 further includes a connector 40 extending from second top 32 to a stem portion 33. Connector 40 may be configured (e.g., shaped and dimensioned) to be attached to female component 20. Male component 30 also includes a spiraling thread 34 on an exterior thereof, suitable for screwing male component 30 into a bone or bone piece.

Figure 14:
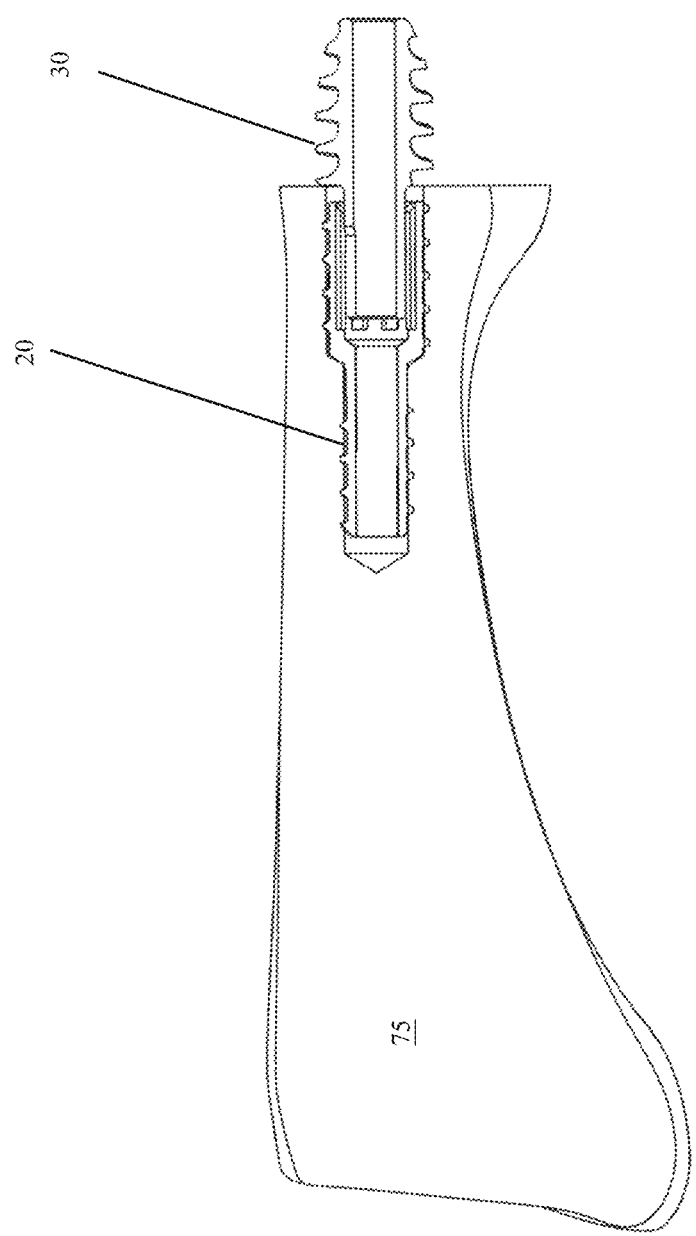
FIG. 14 is a side cross-sectional view of the bone fusion device of FIG. 1 with the male component connected to a bone portion.
Figure 15:
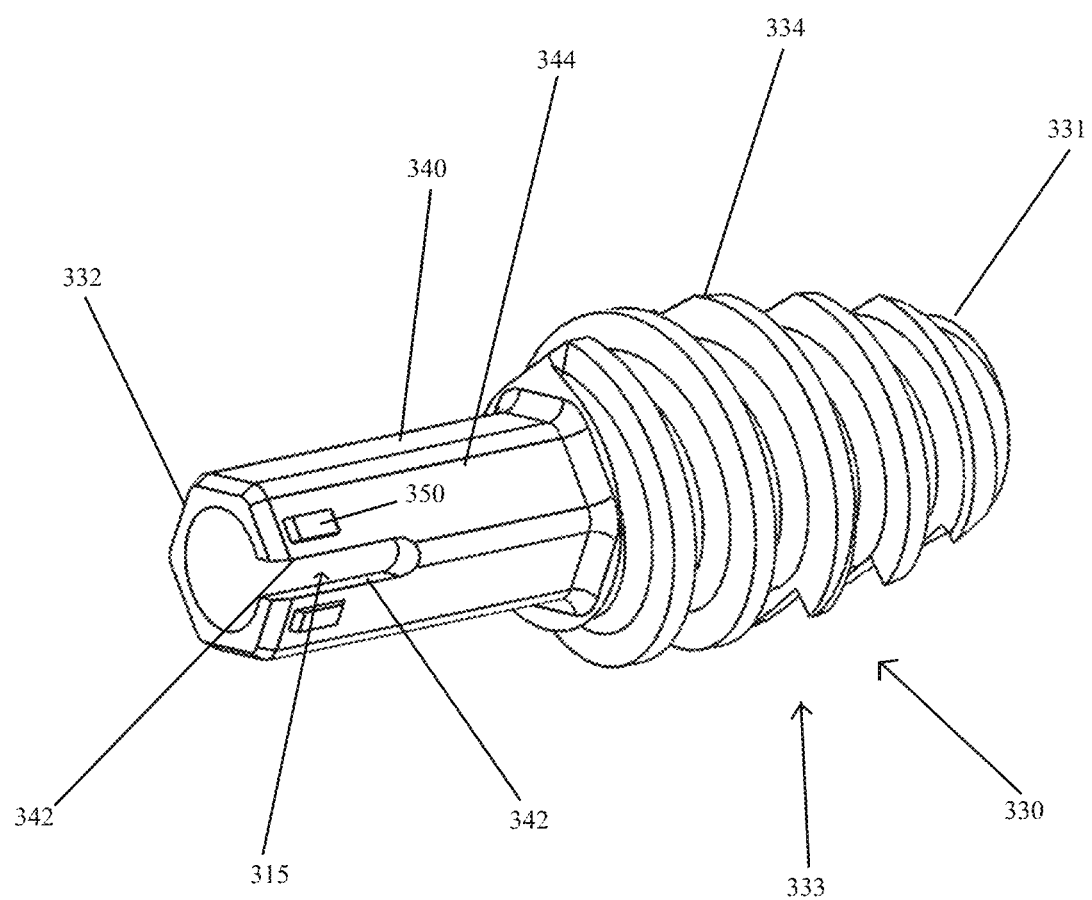
FIG. 15 is a perspective view of an example of a male component of a bone fusion device.

FIG. 14 depicts an example of female component 20 being received in a cavity of a bone 75 and connected to the bone via spiraling thread 24 and male component 30 being connected to the female component and extending therefrom. In an example, male component 30 may be received in, and connected to, a different bone or bone piece (not shown) prior to being connected to female component 20 as depicted.

Female component 20 and male component 30 may independently be cylindrical or conical, or any combination thereof. Where the illustrated embodiments show spiraling threads as means to anchor a male component or female component to a bone, alternate anchoring means may be used. Where present, the spiraling threads can be of any type known in the art for screwing into a bone. Thus, in some embodiments, the spiraling thread is a continuous spiraling thread. In other embodiments, the spiraling thread allows self-tapping and/or self-threading.

In an embodiment, the spiraling threads may be continuous. In yet another embodiment, the spiraling threads may spiral in the same direction so that when the device is screwed into opposing bone surfaces and coupled, the opposing pitch of the threads in the bone prevents the device from unscrewing.

The embodiments described herein are not limited to any particular pitch of one rotation of the continuous spiraling thread. For example, the pitch may be 5 mm or greater, 4 mm, 3 mm, 2 mm, 1 mm, or any distance in between the aforementioned distances.

Figure 2:
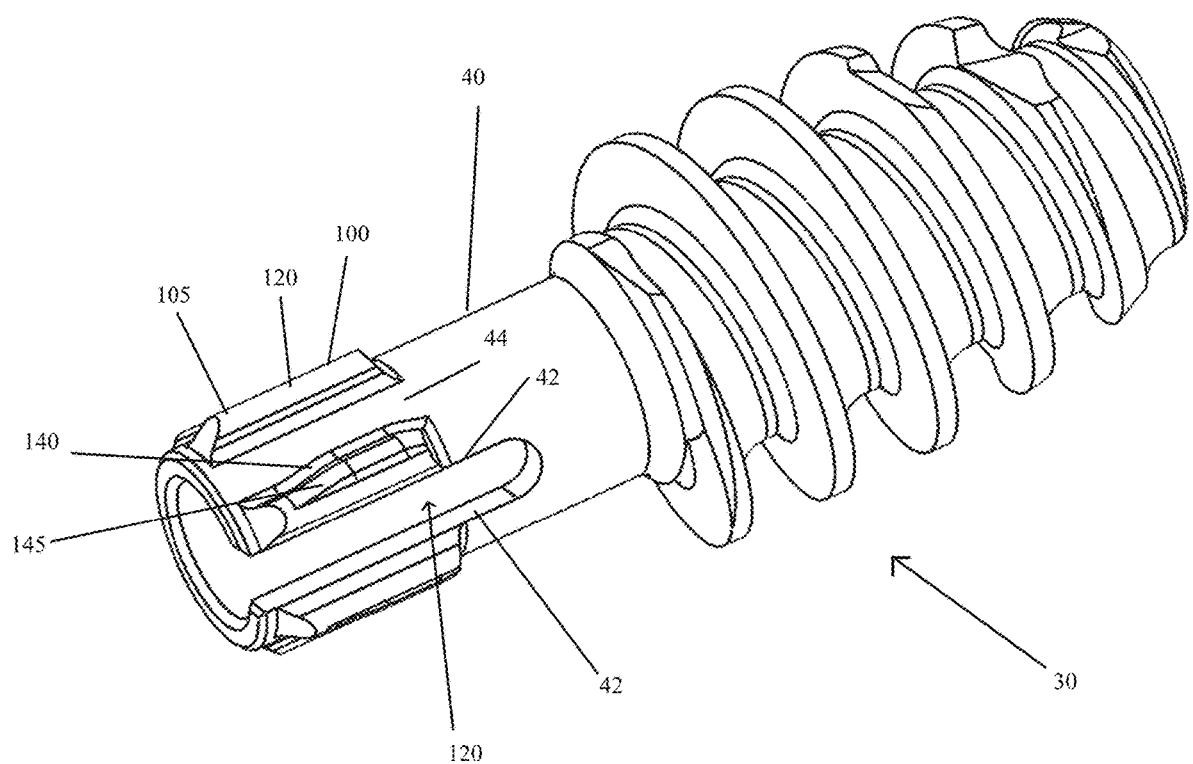
FIG. 2 is a perspective view of a male component of the bone fusion device of FIG. 1.
Figure 3:
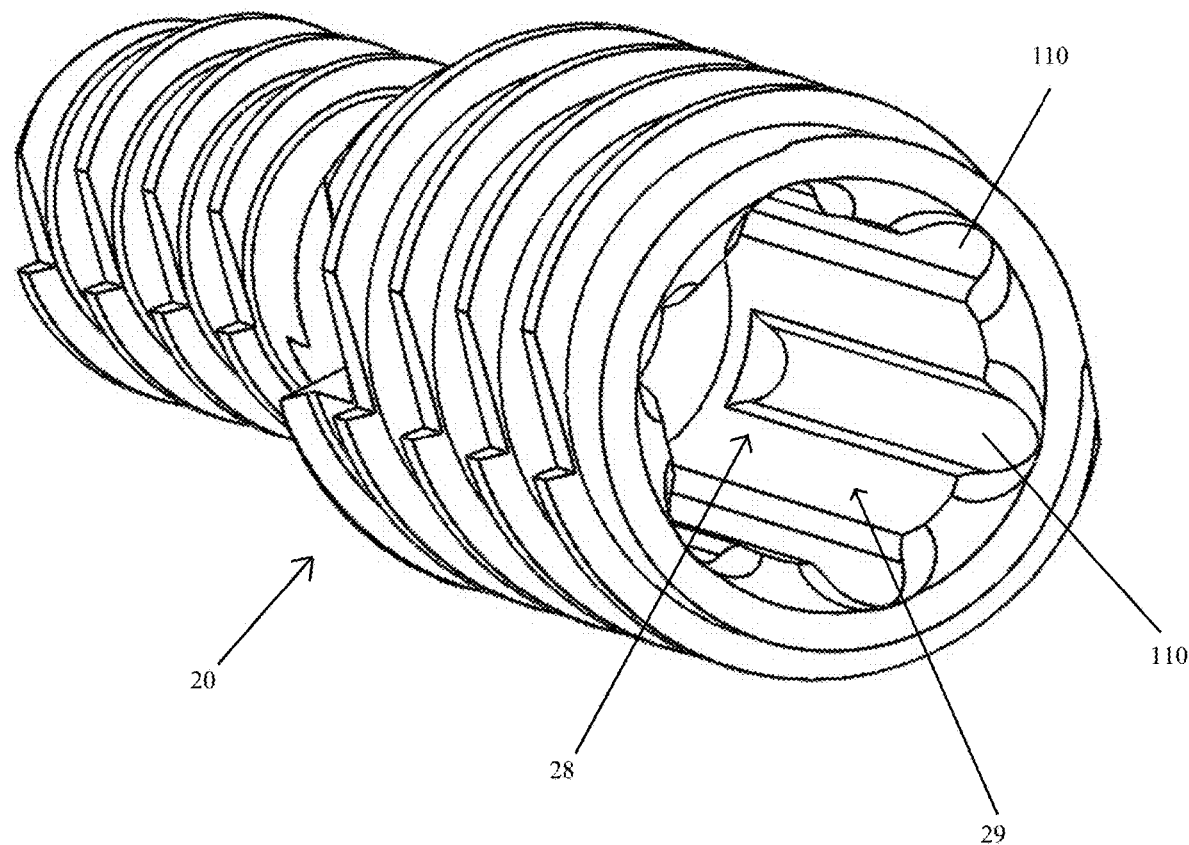
FIG. 3 is a perspective view of a female component of the bone fusion device of FIG. 1.
Figure 4:
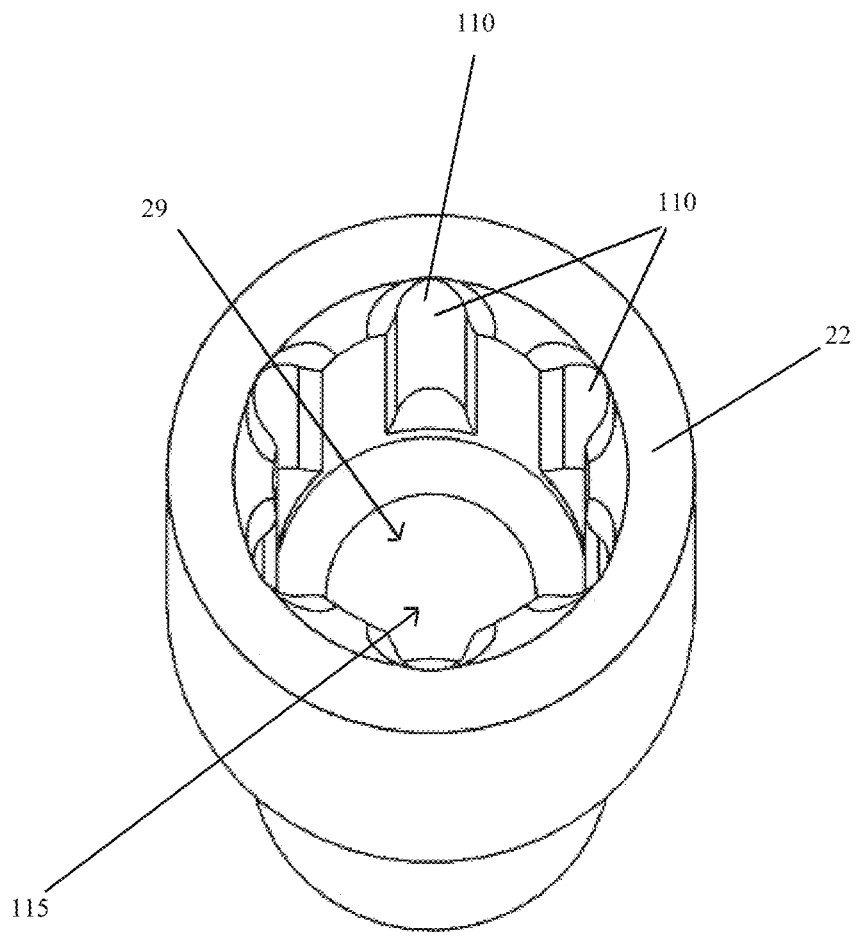
FIG. 4 is a perspective view of an end of the female component of FIG. 3.

Connector 40, as shown in FIGS. 1-2, may include a plurality of lobes, projections or ridges 100 which may be configured (e.g., shaped and dimensioned) to be received in receiving recesses 110 (FIGS. 3-4) of female component 20 to engage or connect the male and female components to each other. Connector 40 may include an axially extending slot 120 bounded by axially extending surfaces 42. Ridges 100 may extend radially outwardly from an inner cylindrical portion 44 of connector 40.

Receiving recesses 110 (FIGS. 3-4) may include a plurality of axially extending portions shaped symmetrically (e.g., evenly spaced circumferentially) to each other surrounding a central cavity 115 of cavity 29. Central cavity 115 may be configured to receive connector 40 minus ridges 100 (e.g. inner cylindrical portion 44), and receiving recesses 110 may be configured (e.g., shaped and dimensioned) to receive ridges 100.

Figure 5:
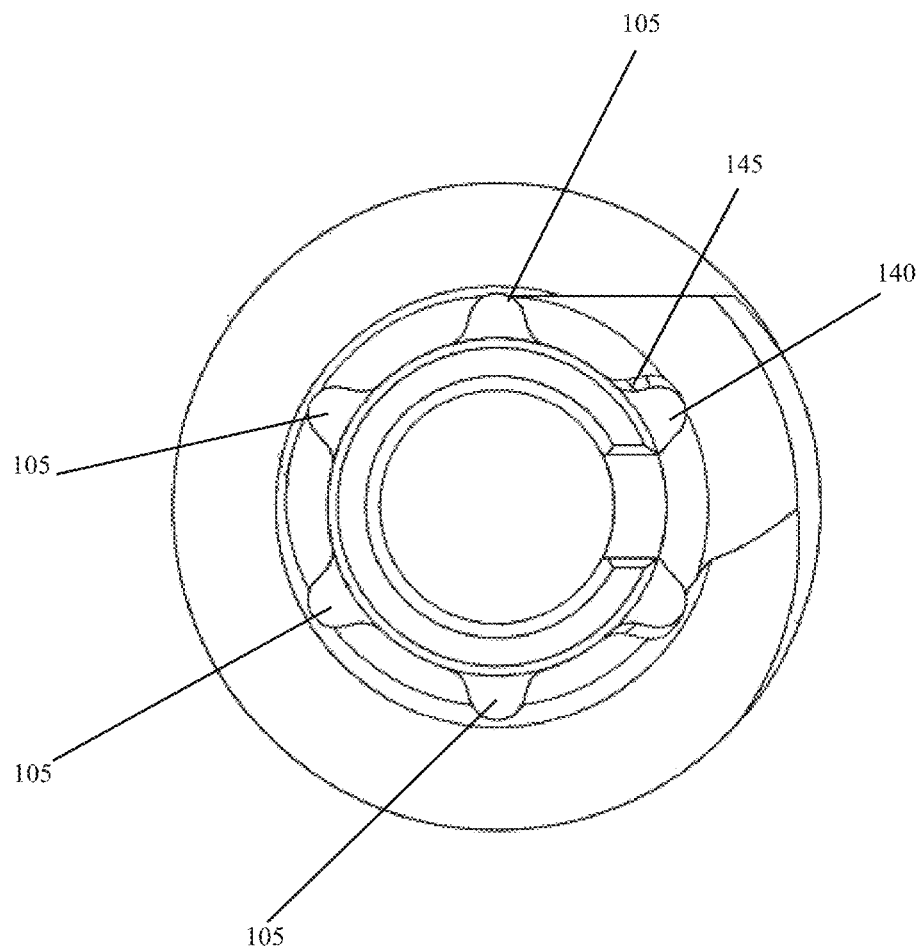
FIG. 5 is a side view of the male component of FIG. 1.
Figure 6:
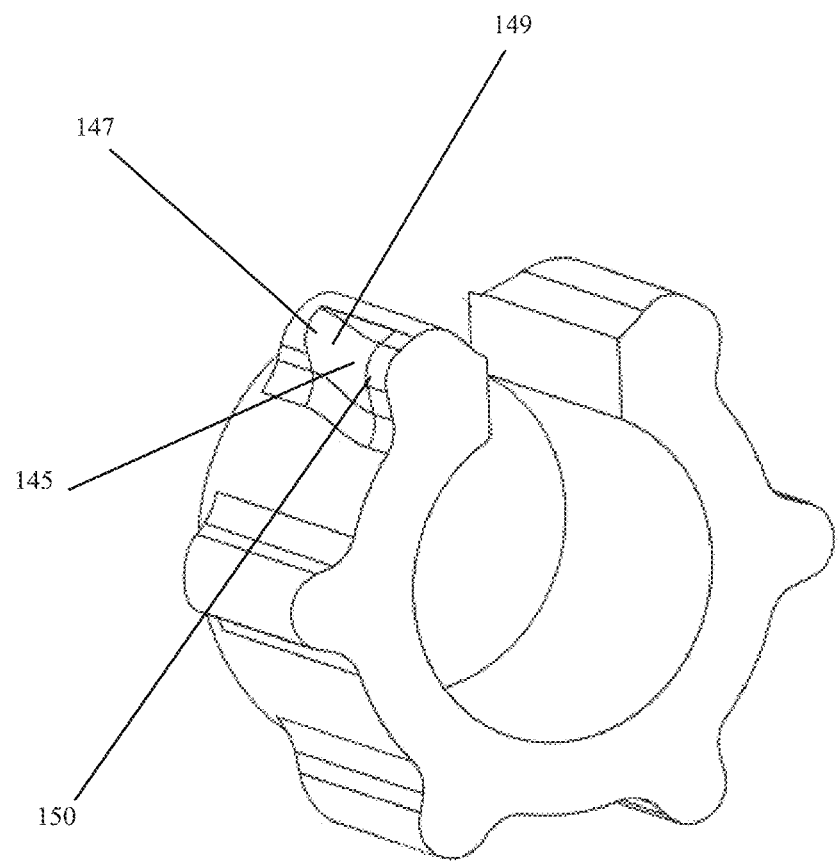
FIG. 6 is a perspective view of a portion of the male component of FIG. 2.

Ridges 100 may include a rounded top portion 120 configured (e.g., shaped and dimensioned) to be received in receiving recesses 110 having complementary shapes as indicated above. Connector 40 may include one or more ridges (e.g., ridges 100) projecting radially outwardly to engage one or more of receiving recesses 110 to facilitate engagement of male component 30 with female component 20. As depicted in FIGS. 2, 5 and 6, for example, engaging ridges 105 of ridges 100 may be symmetric to each other in cross-sectional shape relative to the axis of device 10 and may be received in receiving recesses 110 such that a clearance or space may exist between engaging ridges 105 and inner surfaces 109 bounding recesses 110. Locking ridges 140 of ridges 100 may be located on opposite circumferential sides (i.e., surfaces 42) of slot 120. Locking ridges 140 may have a different axially cross-sectional shape (e.g., may have a larger circumferential dimension) relative to engaging ridges 105 such that locking ridges 140 may contact inner surfaces 109 of female component 20. Each of locking ridges 140 may include a ramp 145 such that locking ridges have a larger cross-section than engaging ridges 105.

As depicted in FIGS. 2, 5 and 6, for example, ramp 145 may include a narrowed portion 147 and a wider portion 150 with an inclined portion 149 therebetween. Narrowed portion 147 may have a smaller dimension in a circumferential and/or radial direction than a dimension of wider portion 150 in the circumferential and/or radial direction. As connector 40 is engaged (e.g., in an axial direction) with female component 20, such that inner cylindrical portion 44 and ridges 100 are received in cavity 29, each of locking ridges 140 may engage female component 20 such that narrowed portion 147 first contacts inner surfaces 109 followed by inclined portion 149 and then wider portion 150. Such contacting of locking ridges 140 with inner surfaces 109 causes a frictional or interference fit therebetween due to a larger circumferential and/or radial dimension of wider portion 150 relative to engaging ridges 105 which may be spaced from inner surfaces 109 bounding recesses 110 as described above.

The contacting of one or more instances of ramp 145 on one or more locking ridges 140 with inner surfaces 109 may cause each instance of ramp 145 to occupy an entire circumferential space of the recess or recesses of recesses 110 where instances of ramp 145 are received to provide the frictional fit or interference. The movement of connector 40 into cavity 29 thus may allow a gradual alignment and frictional fit of ramp 145 with one or more inner surfaces 109 as portions with larger circumferential dimensions (e.g., wider portion 150) are gradually received in recesses 110 as connector 40 is moved axially.

Figure 7:
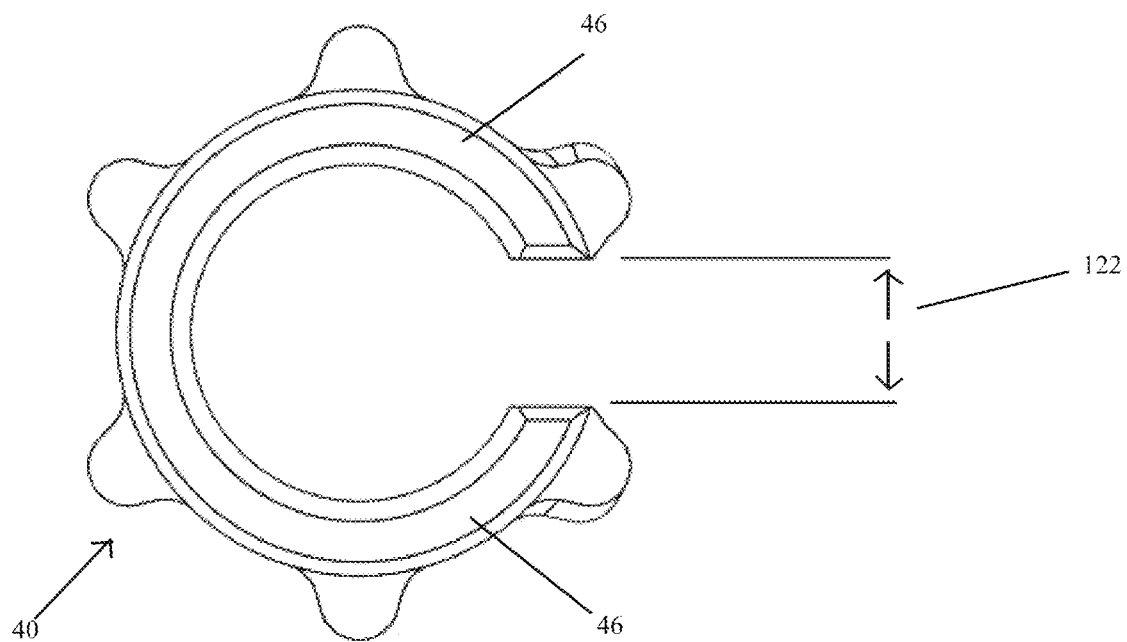
FIG. 7 is a side view of the male component of FIG. 1 in an undeformed state showing a slot at a neutral position.
Figure 8:
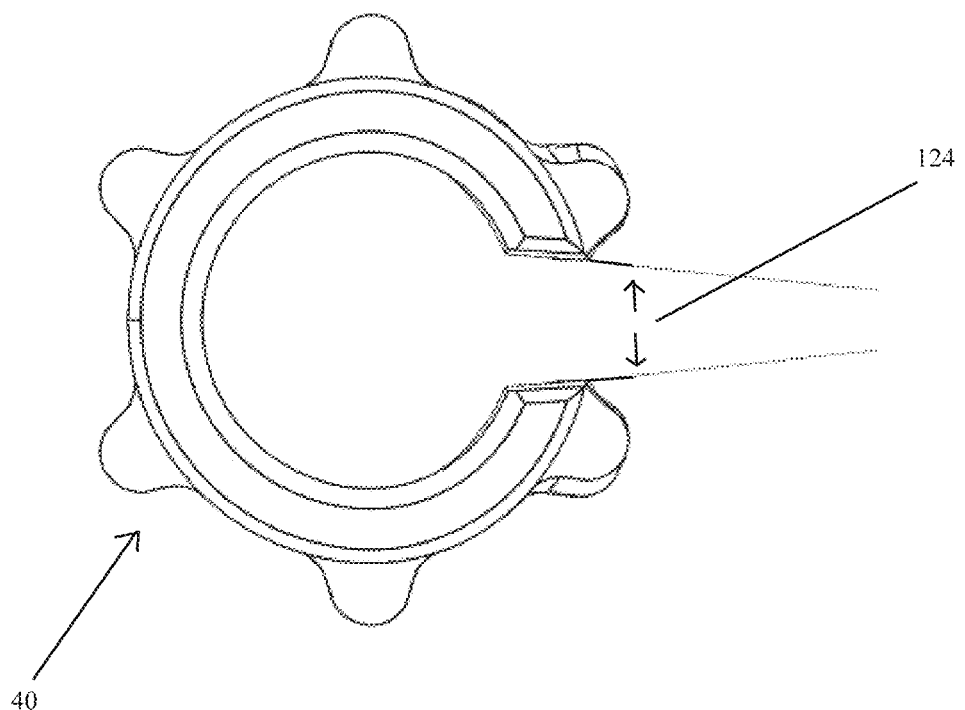
FIG. 8 is a side view of the male component of FIG. 1 in a deformed condition showing a slot thereof in a locked position.

Also, the engagement of one or more instances of ramp 145 with one or more inner surfaces (e.g., inner surfaces 109) may cause a deformation of connector 40 from a neutral position depicted in FIG. 7 to a deformed condition depicted in FIG. 8 such that slot sides (i.e., axially extending surfaces 42) of slot 120 move toward each other to decrease a circumferential dimension of slot 120 due to a deformation of deformation zones 46 of connector 40. Such deformation zones may elastically deform (e.g., radially inwardly) while a remainder of connector 40 may remain in an undeformed state. For example, a neutral slot circumferential dimension 122 (FIG. 7) may be larger than a deformed slot circumferential dimension 124 (FIG. 8).

Connector 40 may be elastically deformable in such deformation zones (or elsewhere) to allow the decrease in the circumferential dimension (i.e., between neutral slot circumferential dimension 122 and deformed slot circumferential dimension 124) while the potential energy of an elastic return of connector 40 may provide or contribute to the frictional or interference fit between connector 40 and female component 20 (e.g., via an engagement of inner cylindrical portion 44 and inner surfaces 109) as described above.

Each of locking ridges 140 may include an instance of ramp 145 located on opposite sides of each of locking ridges 140 relative to slot 120 such that each ramp 145 extends (e.g., circumferentially and radially) away from slot 120. Thus, engagement of each instance of ramp 145 with inner surface 109 bounding a particular recess of recesses 110 may cause movement of locking ridges 140 circumferentially toward each other and cause the deformation of connector 40 (e.g., radially inwardly) such that a circumferential dimension of slot 120 decreases as described above.

In another example, connector 40 could include one locking ridge (e.g., one of locking ridges 140) or more than two such locking ridges with a remaining portion of the ridges (e.g., ridges 100) having smaller circumferential dimensions such that space or clearance may exist between such ridges and inner surfaces (e.g., inner surfaces 109) bounding recesses (e.g., recesses 110) of female component 20. Connector 40 may be located or rotated to a desired position of female component 20 and male component 30 after one or both such components are engaged with bone portions and ridges 100 may be received in recesses 110 at such desired location. In other examples, bone fusion device 10 may include more ridges 100 and recesses 110 than depicted to allow a finer adjustment of male component 30 and female component 20 relative to each other, along with bone portions such components may be engaged with.

Figure 28:
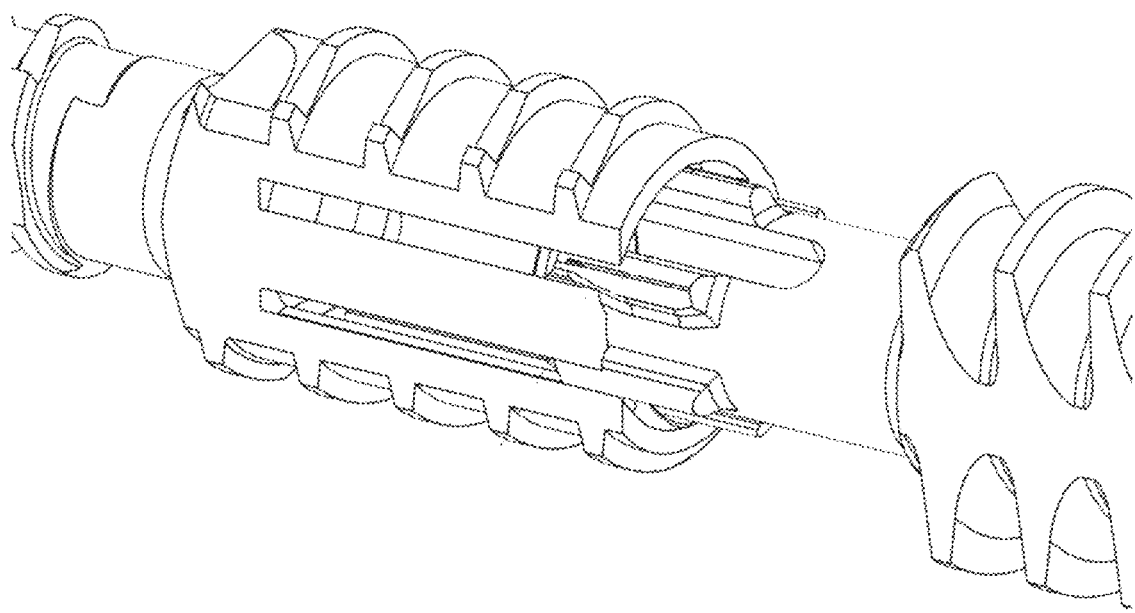
FIG. 28 is a perspective view of a connector portion of the male component engaging the female component of FIG. 1.
Figure 29:
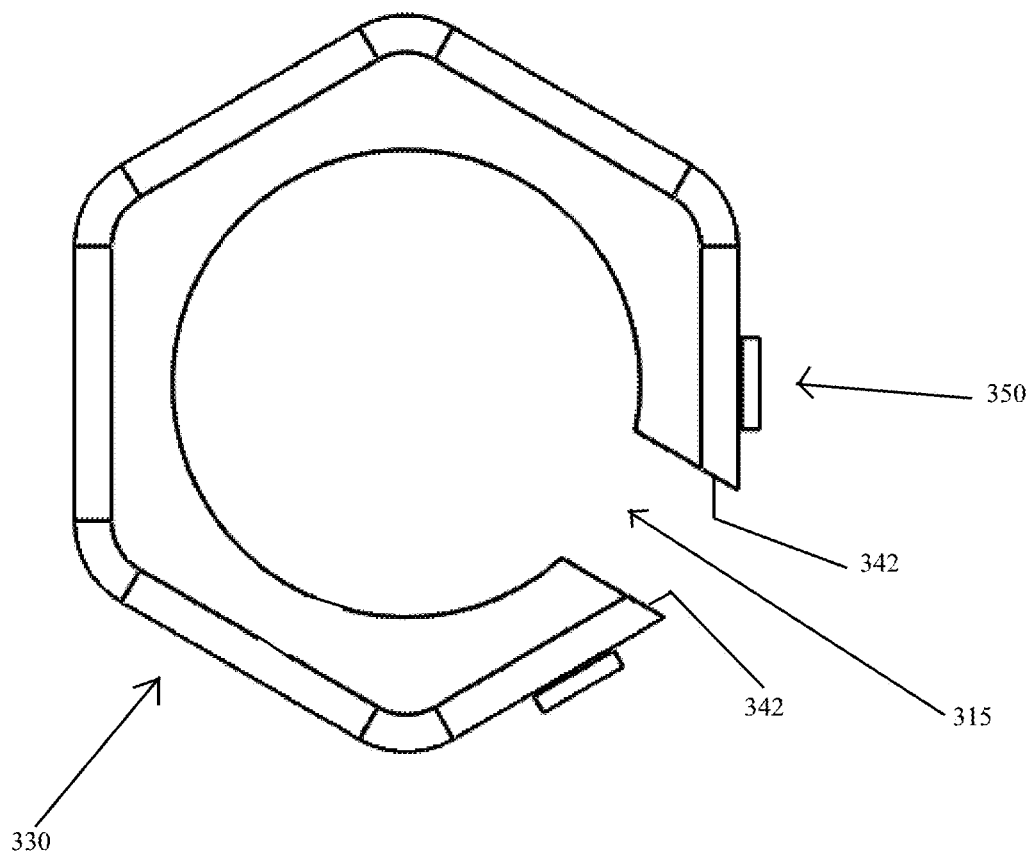
FIG. 29 is a side view of the male component of FIG. 15.

FIG. 28 shows bone fusion device 10 after connector 40 of male component 30 has been inserted into cavity 29 of female component 20. When bone fusion device 10 is the state as depicted, the bones that male component 30 and female component 20 have been screwed into are effectively coupled or fused together. Connector 40 is held and locked within the female component by the frictional fit or interference described above.

In another example not depicted, ridges similar to ridges 100 could be located on an interior surface, similar to inner surface 109, of a female component while a male component may include recesses, similar to recesses 110, on a connector, similar to connector 40, of a male component such that the male and female components may engage to reversibly connect via a friction fit similar to ridges 100 and recesses 110 described above. Also, female component 20 and male component may be formed (e.g., via molding, casting, machining or 3-D printing) of stainless steel, titanium, PEEK, or other biofriendly materials having the structure needed to connect bone portions as described herein.

In a further example not depicted, a connector may be similar to connector 40 except that slot 120 may be omitted particularly in the case of low stiffness materials which may allow deformation (e.g., radial inward deformation) as described above but without the need for such slot.

The frictional fit described above between female component 20 and male component 30 may resist movement due to radial and tangential forces. As described, a ramp (e.g., ramp 45) may cause movement and deformation of a connector (e.g., connector 40) in a circumferential and/or radial direction while an axial force provided by the user (e.g., of 10 pounds or less) may provide resistance in an axial direction to provide the frictional fit.

Figure 9:
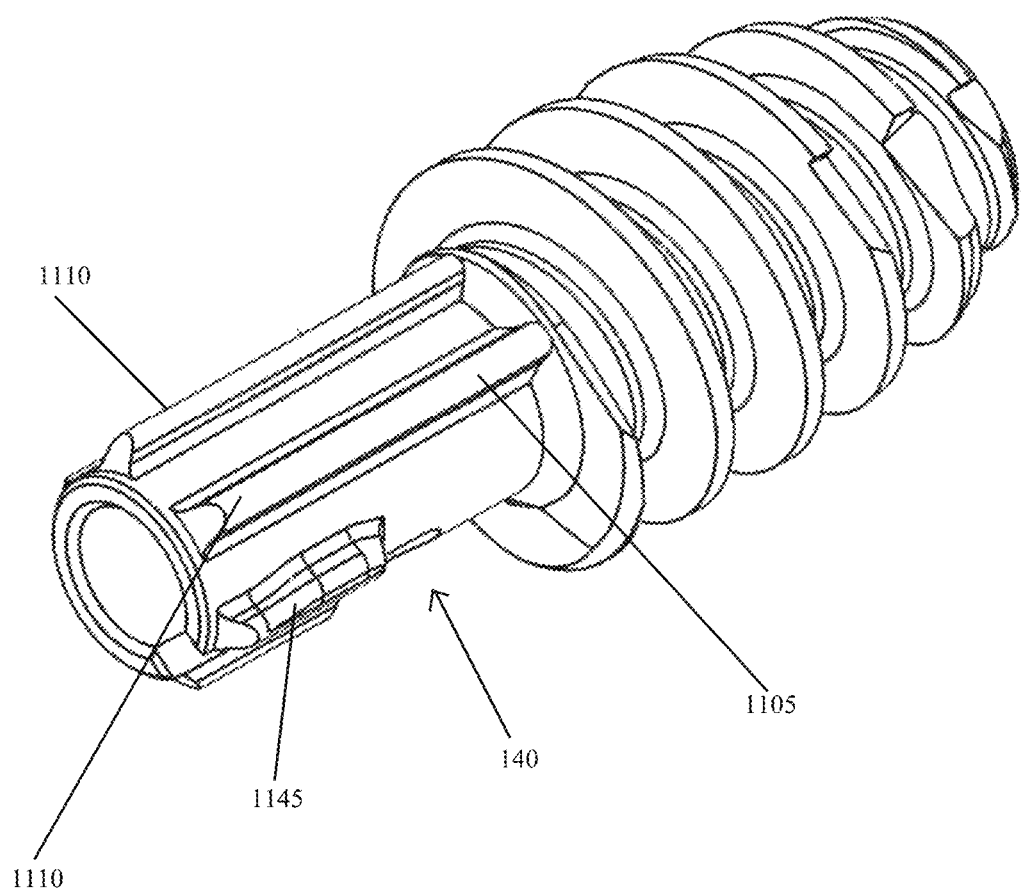
FIG. 9 is a perspective view of another example of a male component engageable with the female component of FIG. 1.

In an example depicted in FIG. 9, a connector 140, similar to connector 40, may include ridges 1100, similar to ridges 100, which include engaging ridges 1105, similar to engaging ridges 105, except that engaging ridges 1105 extend a full axial length of connector 140. Locking ridges 1145 may be identical to locking ridges 145 and have a smaller axial dimension than engaging ridges 1105. Similarly, recesses in a female component (not shown), similar to recesses 110 in female component 30, may have axial lengths at least that of ridges 1105. Connector 140 may thus engage such a female component in a same manner as female component 20 and male component described above.

Figure 10:
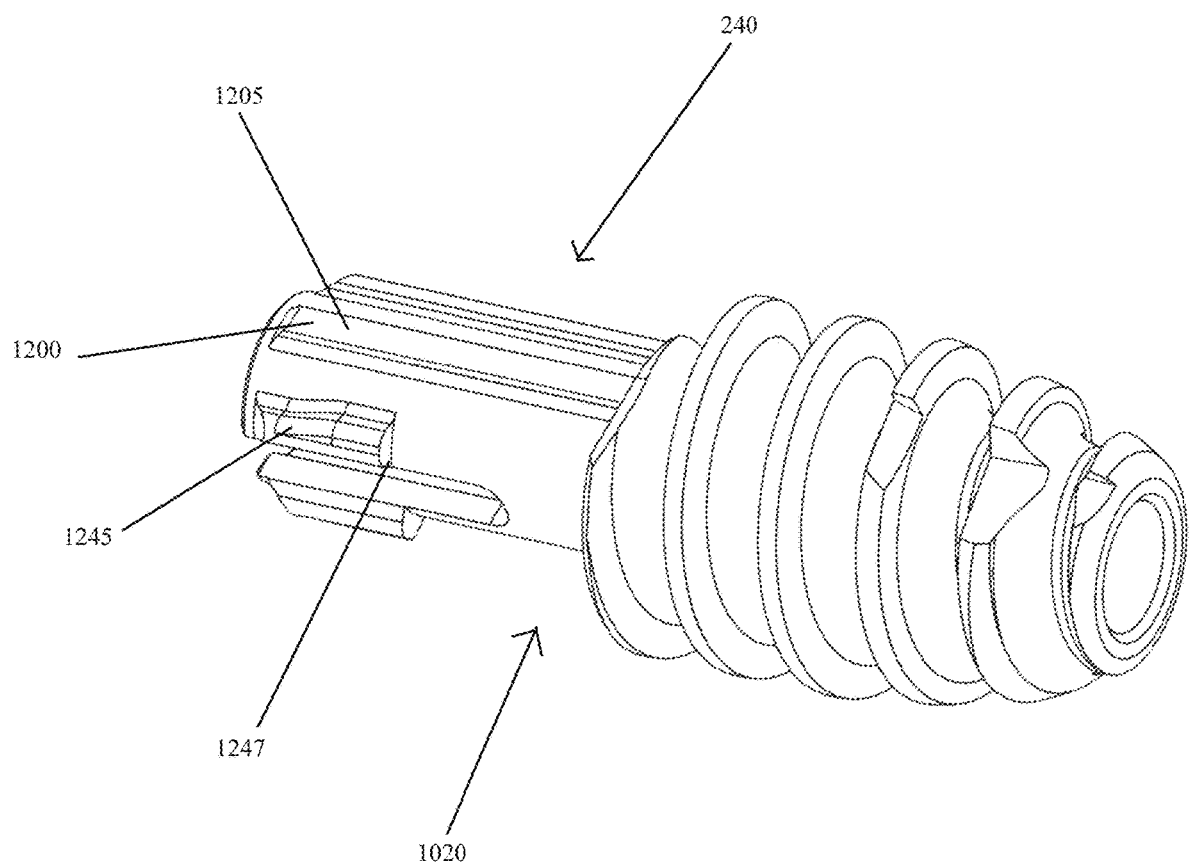
FIG. 10 is a perspective view of an example of a male component of a bone fusion device including locking projections.
Figure 11:
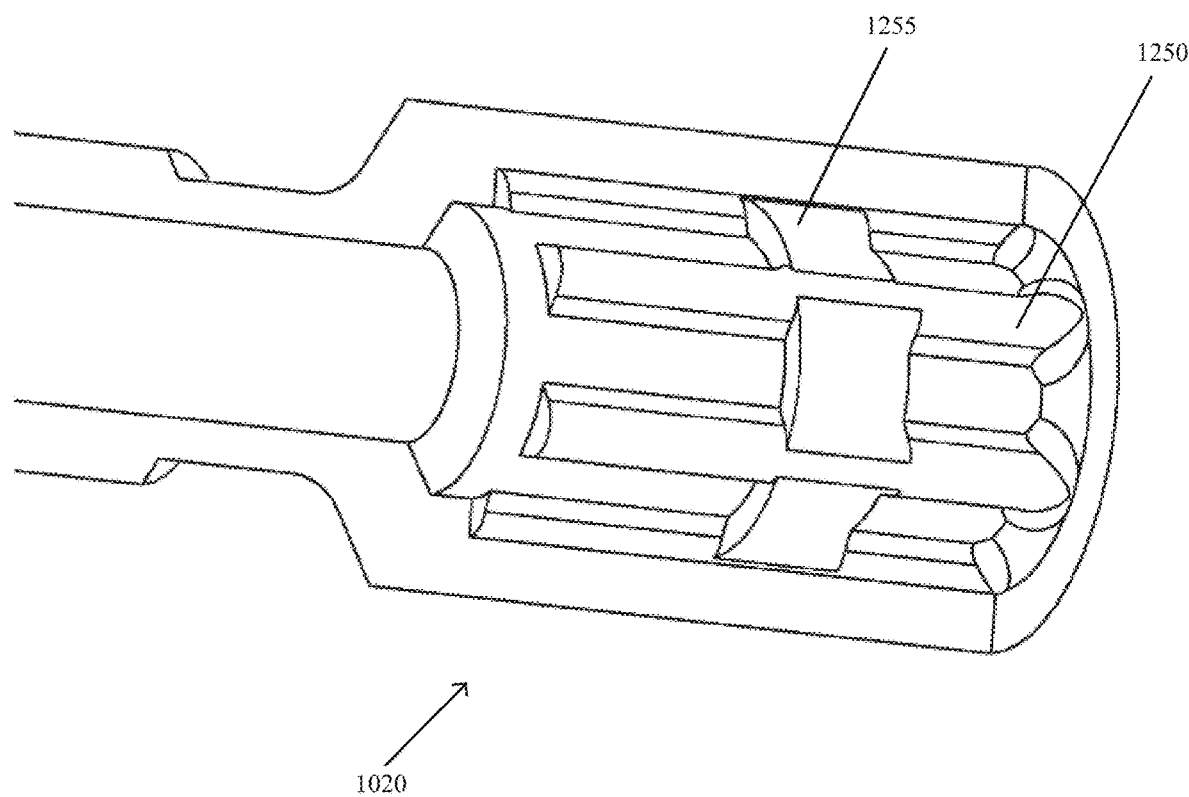
FIG. 11 is a cross-sectional view of a female component of a bone fusion device engageable with the male component of FIG. 10.
Figure 12:
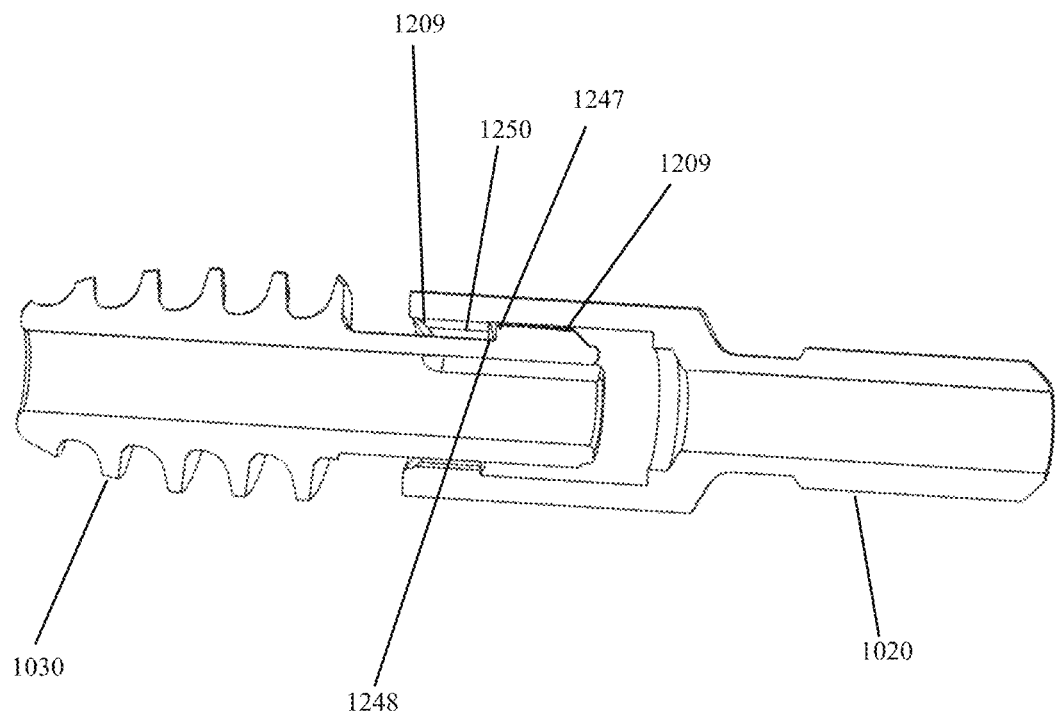
FIG. 12 is a side cross-sectional view of the male component of FIG. 10 and female component of FIG. 11 engaged with each other.

In another example depicted in FIGS. 10-12, a connector 240 of a male component 1030, similar to connector 140, may include ridges 1200, similar to ridges 1100, which include engaging ridges 1205, identical to engaging ridges 1105. Locking ridges 1245 may be similar to ridges 145 except that differing from locking ridges 145, locking ridges 1245 may include a barbed or non-returning end 1247. As described above relative to female component 20 and male component 30, a female component 1020 and male component 1030 may engage with each other such that one or more locking ridges 1245 may be received in one or more recesses 1250 as ridges 100 engage recesses 110 described above. Each of recesses 1250 may have a cavity 1255 in such recess (e.g., recesses 1250) extending radially outwardly configured (e.g., shaped and dimensioned) to receive one of locking ridges 1245. Locking ridges 1245 may be elastically deformed radially inwardly as connector 240 engages female component 1020 and locking ridges are received in recesses 1250. As connector 40 is moved axially toward female component 1020 each of locking ridges 1245 may elastically deform radially outwardly to be received in instances of a cavity 1255, which may be a single cavity (e.g., formed as a circumferential groove) or multiple separate cavities or depressions in each of the recesses (e.g., recesses 1250). Non-returning end 1247 of each of locking ridges 1245 may extend radially, or at an angle relative to a radial direction, such that non-returning end 1247 of each of locking ridges 1245 contacts a complementarily shaped (e.g., radially aligned) stop surface 1248 of an inner surface 1209 bounding cavity 1255 to prevent or inhibit a reverse axial movement to separate female component 1020 and male component 1030 from each other. For example, after connector 240 engages female component 1020 by an axial force being placed between male component 1030 and female component 1020 connector 240 may be deformed radially inwardly until locking ridges 1245 are axially located at one or more instances of recess 1255 wherein connector 240 may elastically return radially outwardly such that locking ridges 1245 are received in one or more instances of recess 1255 and non-returning end 1247 and stop surface 1248 abut one another and inhibit separation of female component 1020 and male component 1030.

In example depicted in FIGS. 15-21, a bone fusion device 310, similar to bone fusion device 10 described above, includes a female component 320 and a male component 330 engageable with each other to connect bone portions attached to such components. Female component 320 is an elongated stem comprising a first end 321, a first top 322, and a cavity 329. Female component 320 also includes a spiraling thread 324 on an exterior thereof, suitable for screwing female component 320 into a bone or bone piece. A stem portion 323 extends from first end 321 to a connecting portion 325 which bounds cavity 329.

Male component 330 is an elongated stem comprising a second end 331 and a second top 332. Male component 330 includes a connector 340 extending from second top 332 to a male component stem portion 333. Connector 340 may be configured (e.g., shaped and dimensioned) to be attached to female component 320. Male component 330 also includes a spiraling thread 334 on an exterior thereof, suitable for screwing male component 330 into a bone or bone piece.

Connector 340 may have a hexagonal cross-sectional shape relative to an axial direction of device 310 in contrast to the cylindrical shape (e.g., inner cylindrical portion 44) with outwardly extending ridges (e.g., ridges 100) of connector 40 described above. Connector 340 may include one or more locking projections or wedges 350 near second top 332 which may be configured (e.g., shaped and dimensioned) to extend radially outwardly from an outer surface 344 of connector 340 and to be received between outer surface 344 and an inner surface 309 of connector portion 325 of female component 320 bounding cavity 329 when female component 320 and male component 330 are engaged.

Inner surface 309 of Female component 320 may be configured (e.g., shaped and dimensioned) to receive connector 340. For example, inner surface 309 may include a plurality of surfaces 311 in a hexagonal shape mirroring outer surface 344 (e.g., having a hexagonal cross-section relative to an axial dimension) of connector 340.

Figure 16:
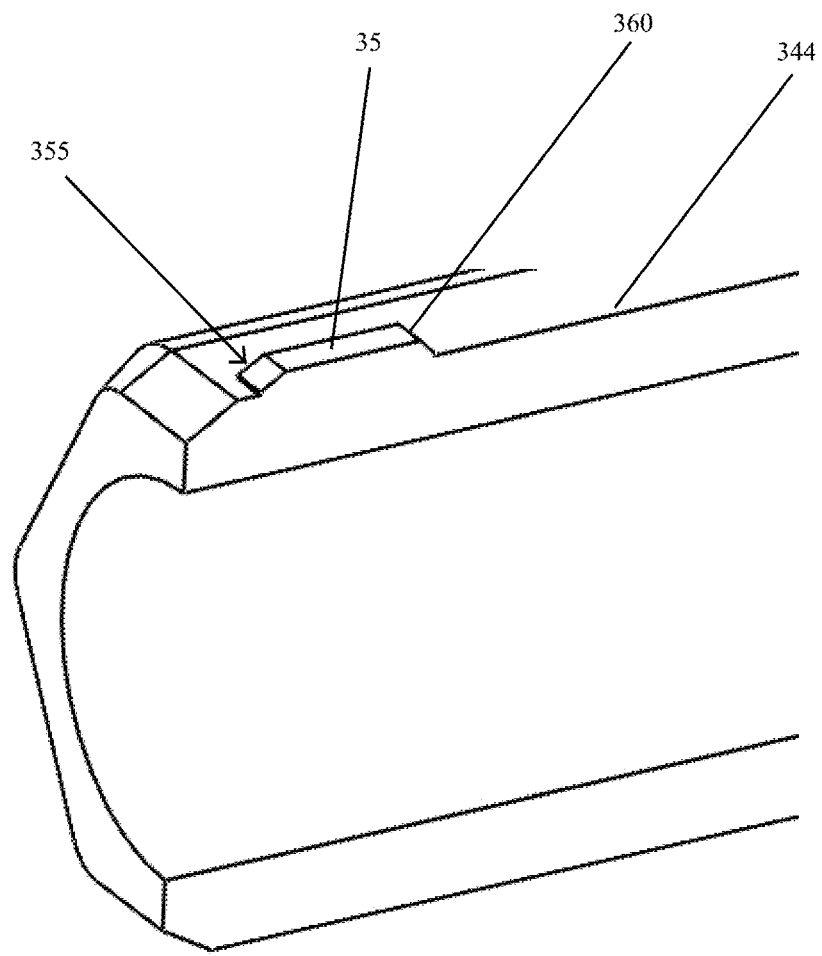
FIG. 16 is a longitudinal cross-sectional view of a portion of a connector of the male component of FIG. 15.
Figure 17:
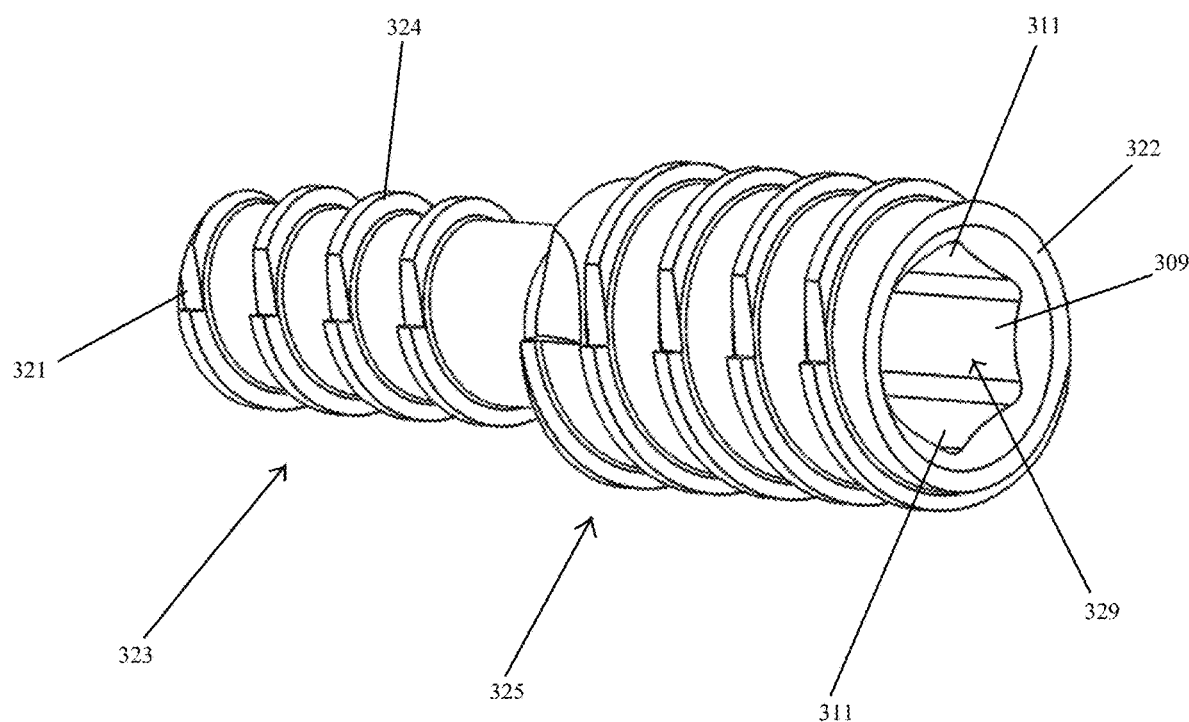
FIG. 17 is a perspective view of a female component engageable with the male component of FIG. 15.
Figure 18:
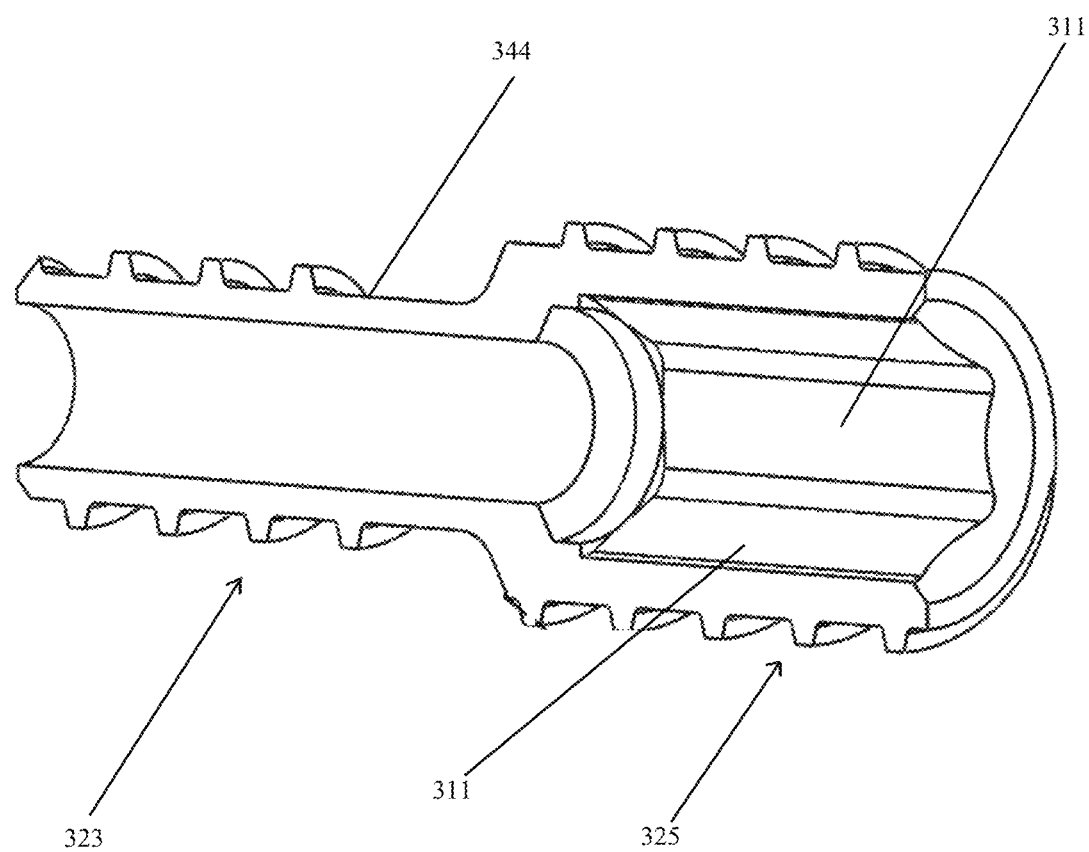
FIG. 18 is a side cross-sectional view of the female component of FIG. 17.
Figure 19:
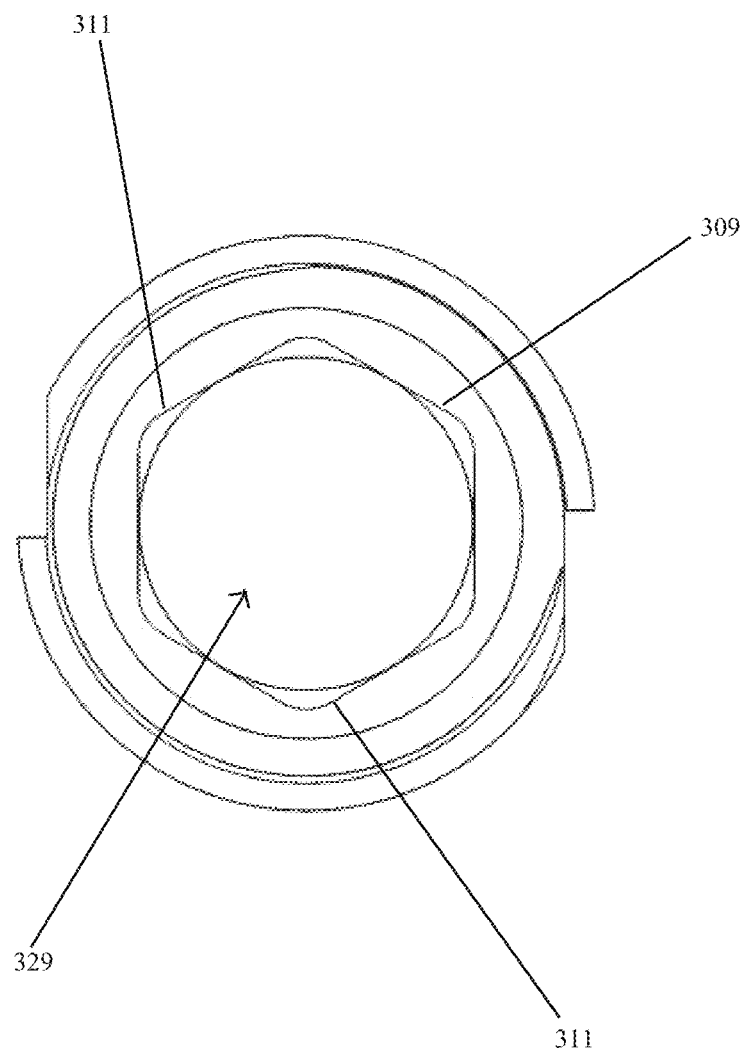
FIG. 19 is a side view of the female component of FIG. 17.
Figure 20:
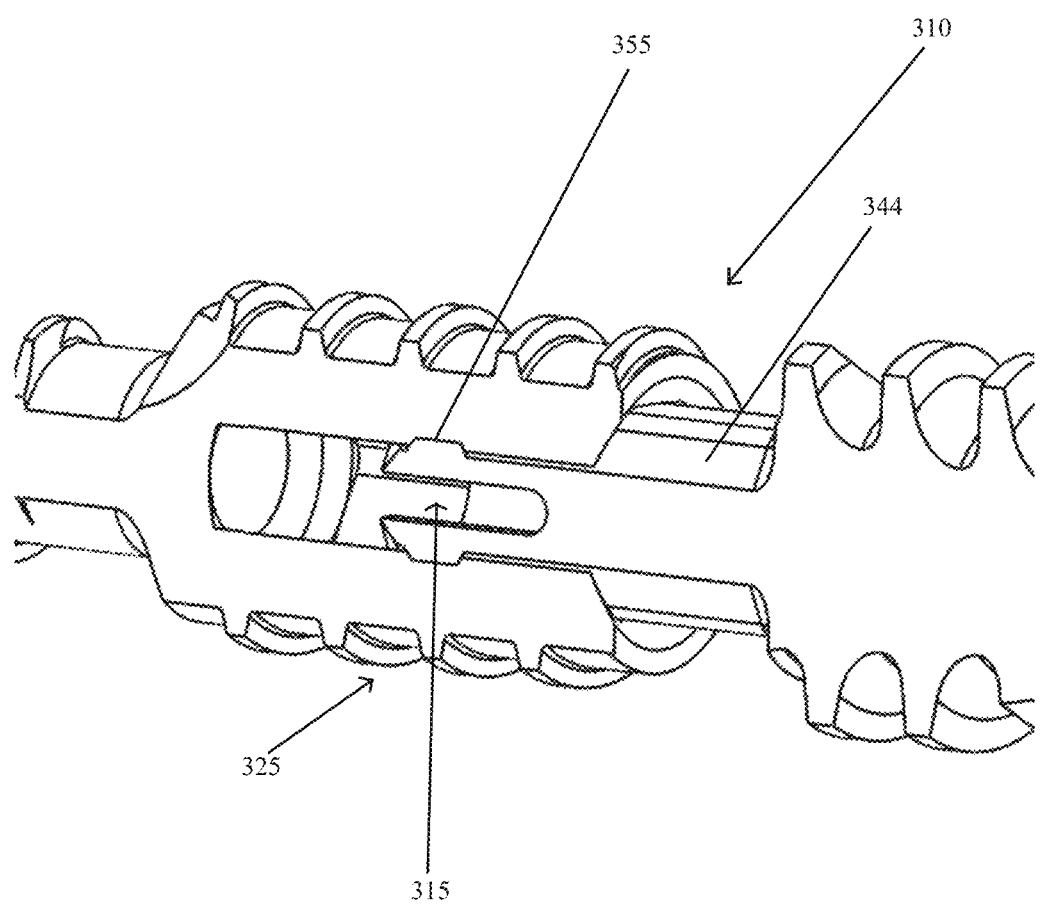
FIG. 20 is a perspective cross-sectional view of an engagement of the male component of FIG. 15 and female component of FIG. 17.
Figure 21:
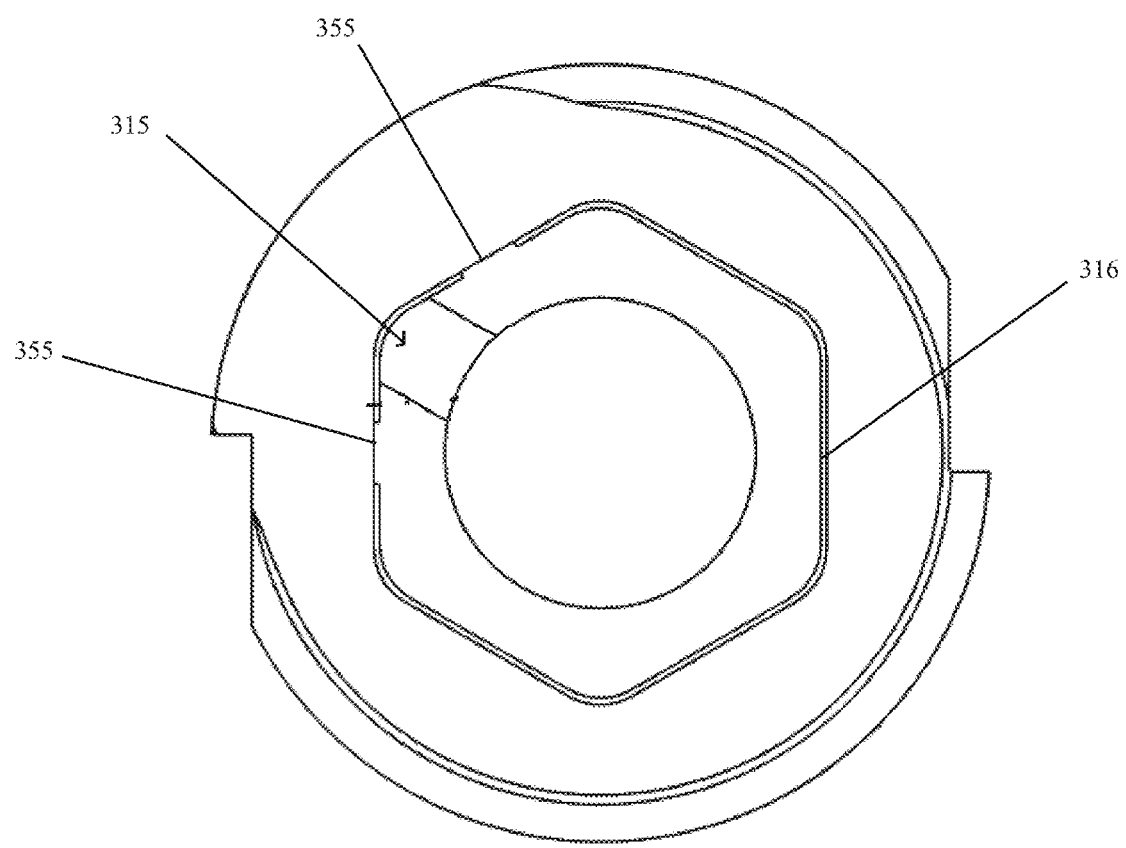
FIG. 21 is a side cross-sectional view of a section of the engagement of male component and female component of FIG. 20.

Connector 340 may include an axially extending slot 315 bounded by axially extending surfaces 342. Wedges 350 may be located on opposite circumferential sides (i.e., surfaces 342) of slot 315. Each of wedges 350 may include a ramp 355 on a longitudinal end thereof closest to second top 332 and a second ramp 360 on an opposite end of ramp 355 as depicted in FIG. 16. Ramp 355 may be an inclined plane connecting a radially outermost surface 357 of ramp 355 with outer surface 344 of connector 340. Similarly, ramp 357 may be an inclined plane extending toward second end 331 and connecting radially outermost surface 357 with outer surface 344. Such ramps promote a frictional engagement or interference between female component 320 and male component 330 when the components are engaged (e.g., via an axial force placed by a user) by allowing inner surface 309 to climb the ramps of wedges 350 such that radially outermost surface 357 of each of wedges 350 contacts inner surface 309 and provides a frictional or interference fit therebetween.

Also, the engagement of wedges 350 with inner surface 309 described above may cause a deformation of connector 340 from a neutral position to a deformed condition such that slot sides (i.e., axially extending surfaces 342) of slot 315 move toward each other to decrease a circumferential dimension of slot 315 due to a deformation of deformation zones of connector 340, as described above relative to slot 120 of connector 40. Such deformation zones may elastically deform (e.g., radially inwardly) while a remainder of connector 340 may remain in an undeformed state. For example, a space 316 may remain between outer surface 344 and inner surface 309 on an opposite side of device 310 relative to slot 315.

Connector 340 may be elastically deformable in such deformation zones (or elsewhere) to allow the decrease in the circumferential dimension (i.e., between a neutral slot circumferential dimension and a deformed slot circumferential dimension) while the potential energy of an elastic return of connector 340 may provide a frictional or interference fit between connector 340 and female component 320 via wedges 350 being located therebetween as described above.

In another example depicted in FIGS. 22-26, 15-21, a bone fusion device 410, similar to bone fusion device 310 described above, includes a female component 420 and a male component 430 engageable with each other to connect bone portions attached to such components. Female component 420 (FIGS. 24-25) may be an elongated stem comprising a first end 421, a first top 422, and a cavity 429. A stem portion 423 extends from first end 421 to a connecting portion 425 which bounds cavity 429. Female component 420 also includes a spiraling thread 424 on an exterior thereof, suitable for screwing female component 420 into a bone or bone piece.

Male component 330 may be an elongated stem comprising a second end 431 and a second top 432. Male component 430 includes a connector 440 extending from second top 332 to a stem portion 433. Connector 440 may be configured (e.g., shaped and dimensioned) to be attached to female component 420. Male component 430 also includes a spiraling thread 434 on an exterior thereof, suitable for screwing male component 430 into a bone or bone piece.

Connector 440 may have a hexagonal cross sectional shape relative to an axial dimension of device 410 in contrast to the cylindrical shape with ridges of connector 40 described above. Connector 440 may include one or more wedges 450 near second top 432 which may be configured (e.g., shaped and dimensioned) to be received between an outer surface 444 of connector 440 and an inner surface 409 of connector portion 425 of female component 420 bounding cavity 429.

Figure 24:
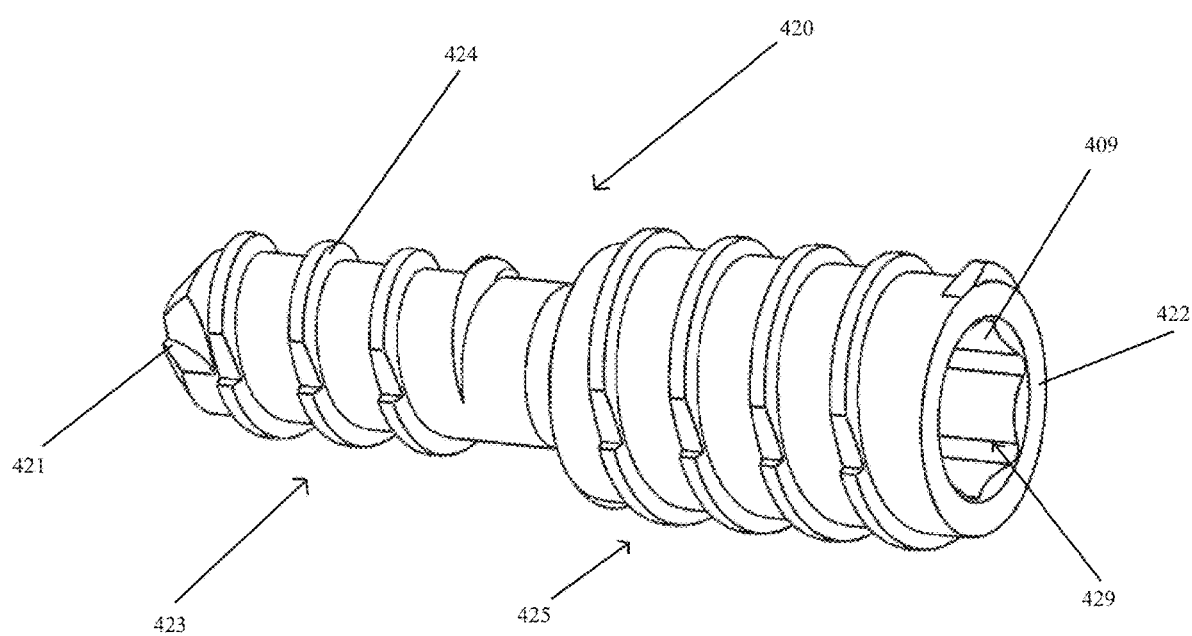
FIG. 24 is a perspective view of an example of a female component engageable with the male component of FIG. 22.
Figure 25:
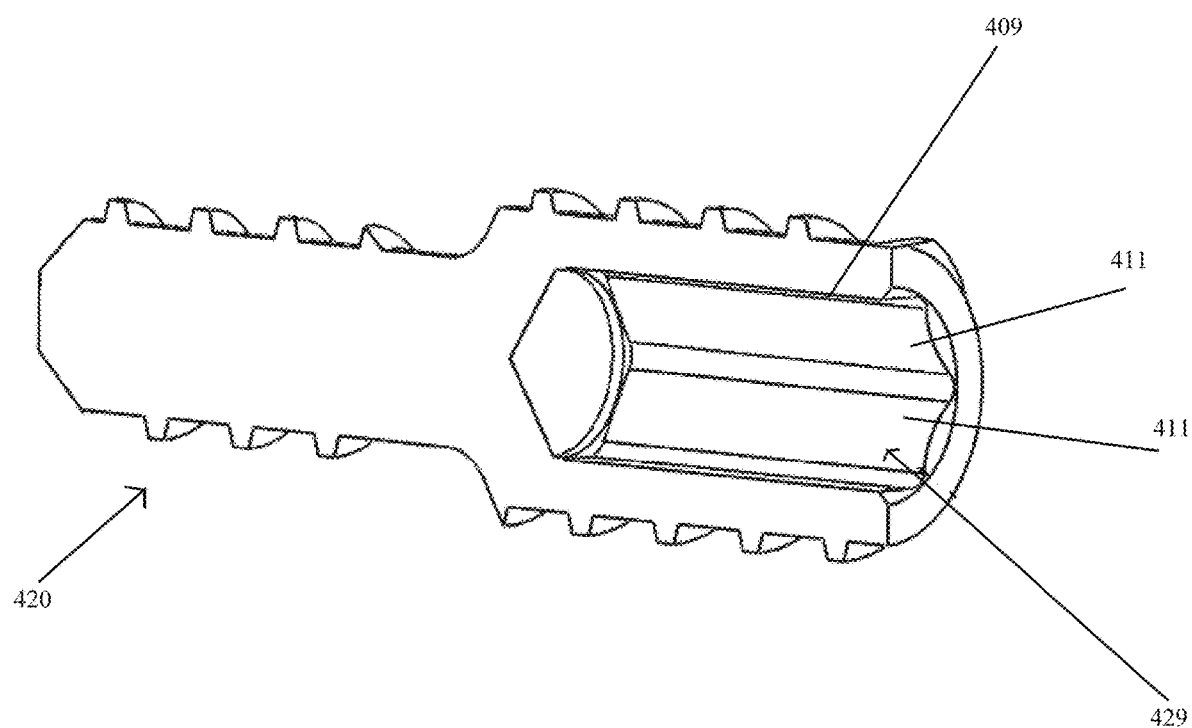
FIG. 25 is a side perspective cross-sectional view of the female component of FIG. 24.
Figure 26:
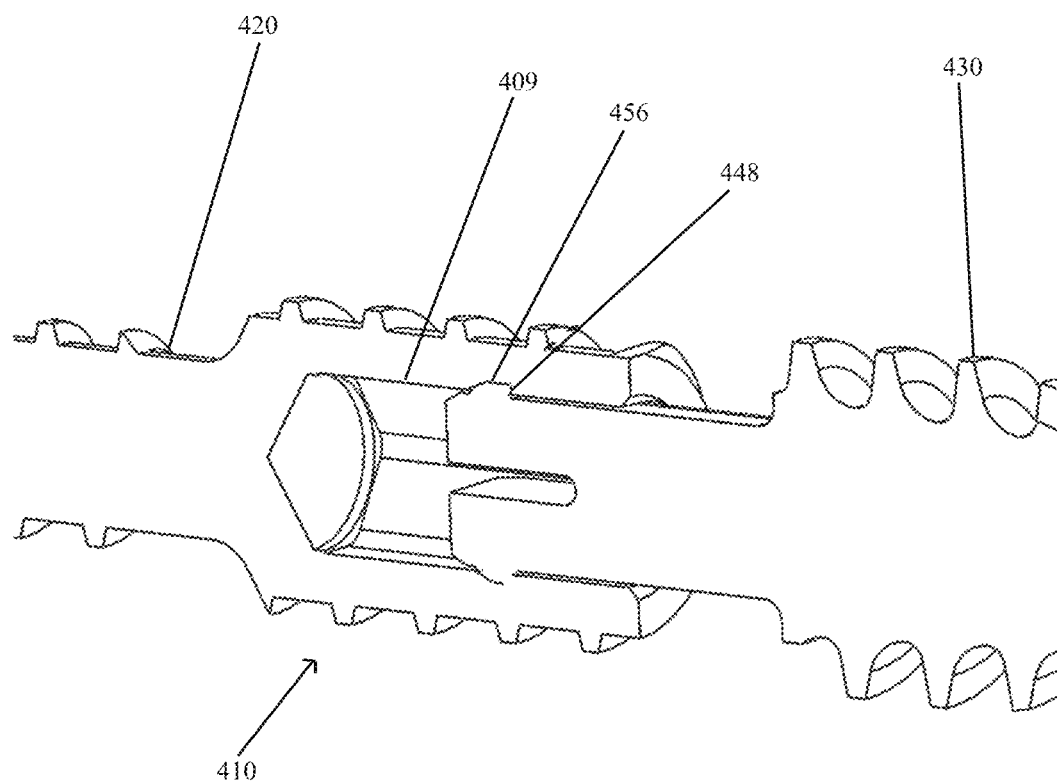
FIG. 26 is a perspective cross-sectional view of engagement of the male component of FIG. 22 and female component of FIG. 24.
Figure 27:
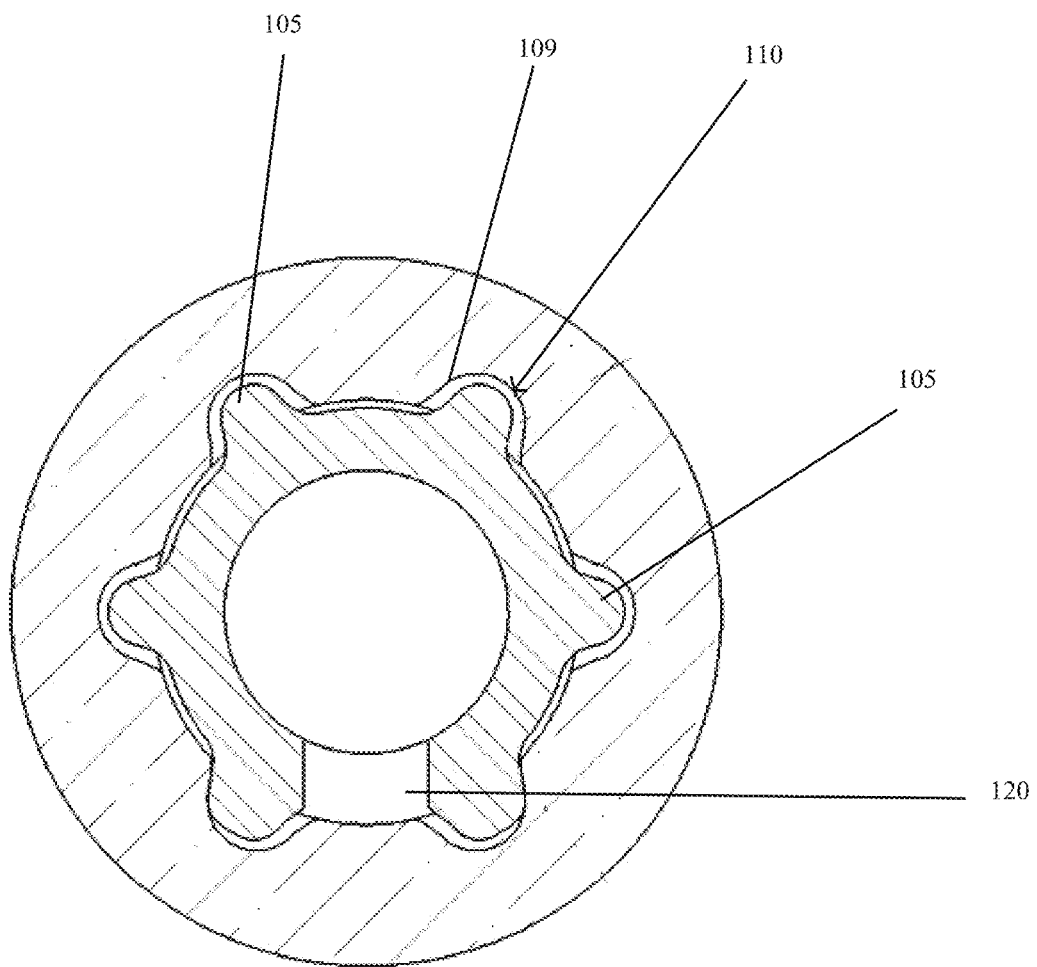
FIG. 27 is a cross-sectional view of the male component and female component of FIG. 1 engaged with each other.

Inner surface 409 of Female component 420 may be configured (e.g., shaped and dimensioned) to receive connector 440. For example, inner surface 409 of connecting portion 425 may include a plurality of surfaces 411 in a hexagonal shape mirroring outer surface 444 (e.g., having a hexagonal cross-section relative to an axial dimension) of connector 440 as depicted in FIGS. 24-26, for example.

Connector 440 may include an axially extending slot 415 bounded by axially extending surfaces 442. Slot 415 may extend through connector 440 from a first side 417 to a second side 419 thereof thereby creating an open space (i.e., slot 415) between a top portion 412 and a bottom portion 414 of connector 440. Wedges 450 may be located on top portion 412 and bottom portion 414 of connector 440, for example, such that top portion 412 and bottom portion 414 may deflect toward each other into slot 415 in response to a force being place on one for more of wedges 350 (e.g., by an axial force during engagement of female component 420 and male component 430). Connector 440 may be elastically deformable such that a deflection of top portion 412 and bottom portion 414 toward each other may create a potential energy in an outward direction that may cause a frictional or interference fit between one or more of wedges 450 and inner surface 409 when female portion 420 and male portion 430 are engaged with each other.

Figure 22:
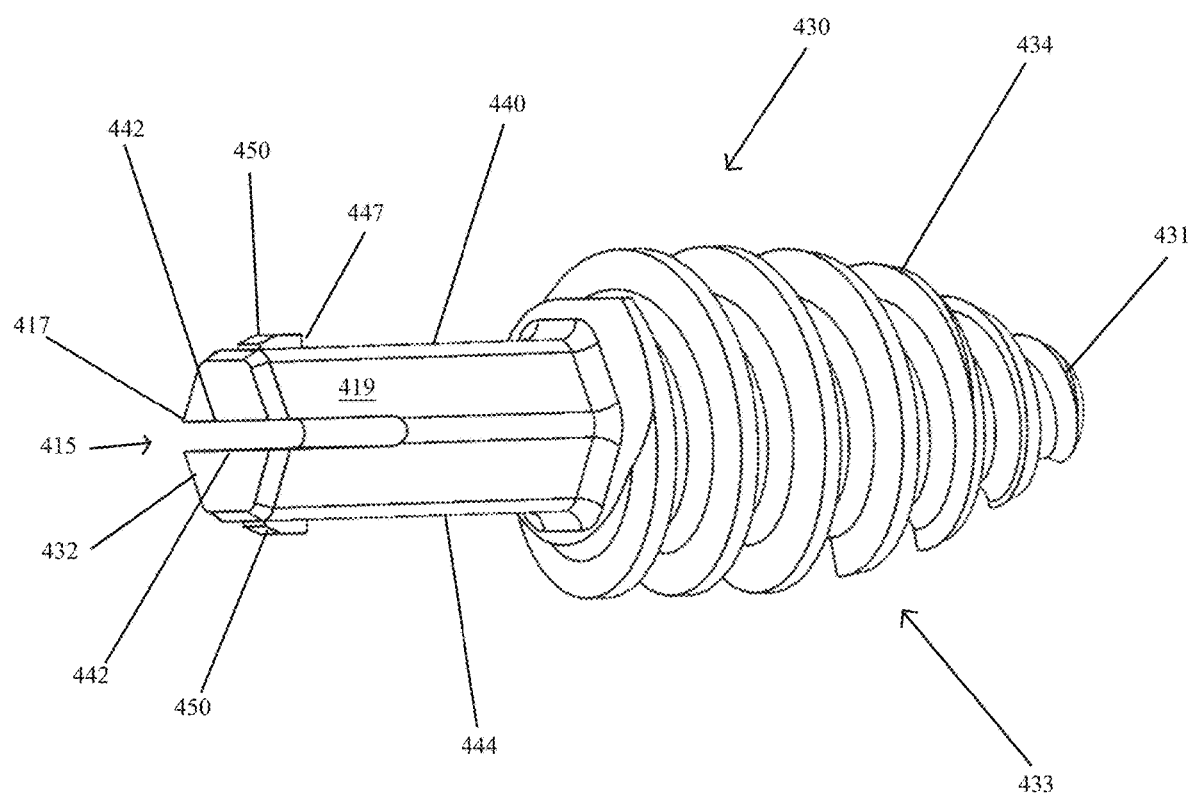
FIG. 22 is a perspective view of an example of a male component of a bone fusion device.
Figure 23:
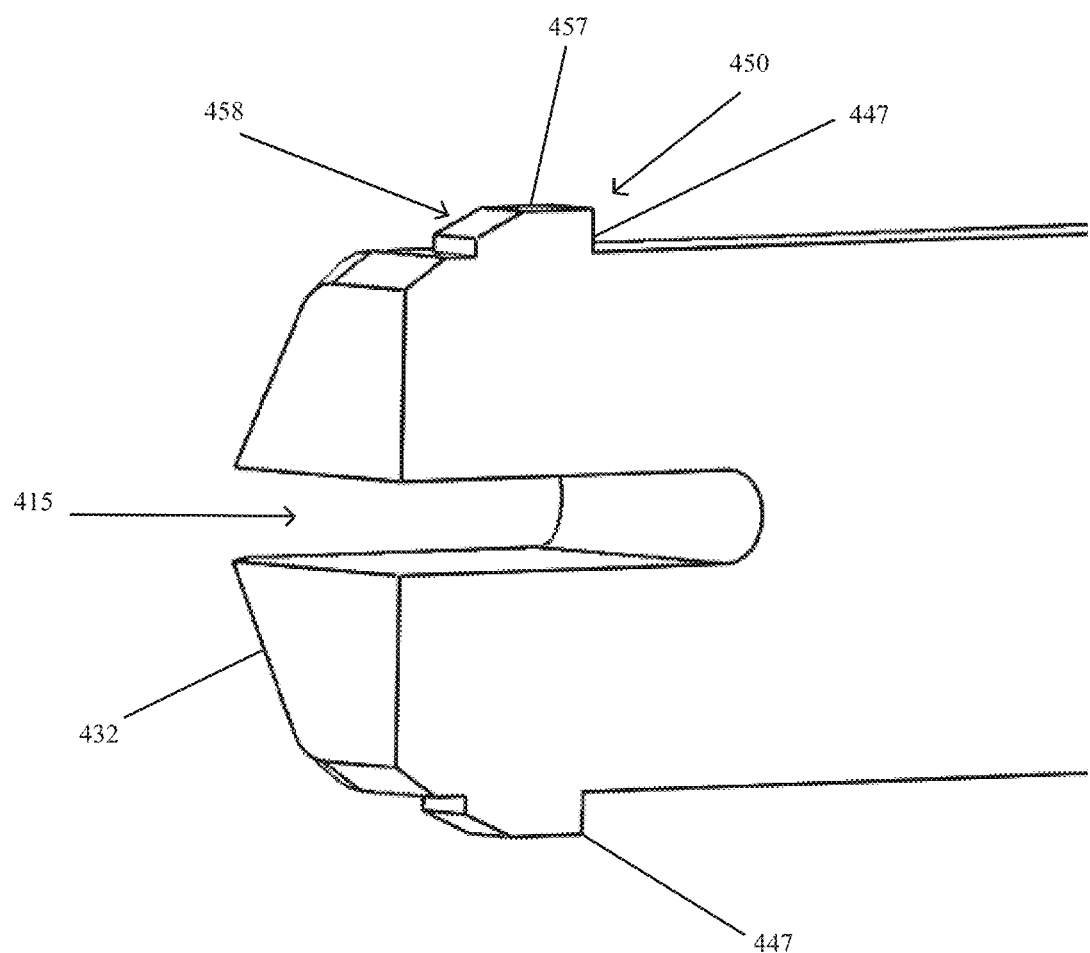
FIG. 23 is a side perspective cross-sectional view of a portion of a connector of the male component of FIG. 22.

Each of wedges 450 may include a ramp 455 on a longitudinal end thereof closest to second top 432 and may include a barbed or non-returning end 447 as depicted in FIGS. 22-23. Ramp 455 may be an inclined plane connecting a radially outermost surface 457 of ramp 455 with outer surface 444 of connector 440. Such ramp may promote a frictional engagement or interference between female component 420 and male component 430 when the components are engaged (e.g., via an axial force of engagement placed by a user) by allowing inner surface 409 to climb the ramps such that radially outermost surface 457 of each of wedges 350 contacts inner surface 309 and provides a frictional or interference fit therebetween.

Also, the engagement of wedges 450 with inner surface 409 described above may cause a deformation of connector 440 from a neutral position to a deformed condition such that slot sides (i.e., axially extending surfaces 442) of slot 415 move toward each other to decrease a circumferential dimension of slot 415 due to a deformation of deformation zones (e.g., in top portion 412 and/or bottom portion 414) of connector 440, as described above relative to slot 120 of connector 40. Such deformation zones may elastically deform (e.g., radially inwardly) while a remainder of connector 440 may remain in an undeformed state.

Connector 440 may be elastically deformable in such deformation zones, or elsewhere along a longitudinal dimension thereof, to allow the decrease in the circumferential dimension (i.e., between a neutral slot circumferential dimension and a deformed slot circumferential dimension) while the potential energy of an elastic return of connector 440 may provide a frictional or interference fit between connector 440 and female component 420 via wedges 450 being located therebetween as described above.

Non-returning end 447 may extend radially, or at an angle relative to a radial direction, such that non-returning end 447 of each of wedges 450 may contact inner surface 409 bounding cavity 429 to prevent or inhibit a reverse axial movement to separate female component 420 and male component 430 from each other. For example, inner surface 409 may include a circumferential groove, cavity or plurality of cavities configured (e.g., shaped and dimensioned) to receive wedges 450 and having a radial surface on a side of such groove closest to top 422 such that non-returning end 447 may contact such side of such groove and axial movement of wedges 450, and connector 440, past such groove may be inhibited to lock female component 420 and male component 430 together.

For example, connector 440 and wedges 450 may be elastically deformed radially inwardly as connector 440 engages female component 420 and wedges 450 are received between inner surface 409 and outer surface 444. As connector 440 is moved axially toward female component 420 each of wedges 450 may elastic deform radially outwardly to be received in instances of a cavity 456, which may be a single cavity (e.g., formed as a circumferential groove) or multiple separate cavities or depressions in inner surface 409. Non-returning end 447 of each of wedges 450 may extend radially, or at an angle relative to a radial direction, such that non-returning end 447 of each of wedges 450 contacts a complementarily shaped (e.g., radially aligned) stop surface 448 of an inner surface 409 bounding cavity 429 to prevent or inhibit a reverse axial movement to separate female component 420 and male component 430 from each other. For example, after connector 440 engages female component 420 by an axial force being placed between male component 430 and female component 420 connector 440 may be deformed radially inwardly until wedges 450 are axially located at one or more instances of recess 456 wherein connector 440 may elastically return radially outwardly such that wedges 450 are received in one or more instances of recess 456 and non-returning end 447 and stop surface 448 abut one another and inhibit separation of female component 420 and male component 430, similar to the above description of the engagement of female component 1020 and male component 1030.

The connectors described above (e.g., connector 40, connector 340, connector 440) may include male components (e.g., male component 30, male component 330, male component 430) and connector portions (e.g., connector portion 425) of female component (e.g., female component 20, female component 320, female component 420) configured to engage with each other such that an axial separation therebetween is prevented or inhibited, and such that movement or rotation between the portions of such connectors may be prevented or inhibited. For example, as described above, a wedge or locking ridge of a connector may cause a frictional or interference fit to inhibit separation between male and female components of a connector. Further, such ridges or wedges may include surfaces shaped to be received in cavities of recesses of inner surfaces of such female connectors to further inhibit separation between the male and female components as described above. Also, an exterior cross-sectional shape of a male component may be complementary relative to an inner surface bounding a cavity or a receiving recess of a female component such that the inner surfaces of the female component contact the outer surfaces of the male portion to inhibit movement therebetween. Such inner surface of a female component and outer surface of a male component may be non-threaded and non-threadingly engageable relative to each other. The connectors, projections, and recesses may extend longitudinally such that the axial cross-sectional shapes are substantially consistent to form substantially cylindrical or substantially flat surfaces forming a polygon (e.g., hexagon) which may allow the male and female components to engage with each other. Accordingly, movement or rotation between bones or bone portions connected to such male and/or female portions may be prevented or inhibited.

As indicted above the bone fusion devices, (e.g., bone fusion device 10, bone fusion device 310, bone fusion device 410) may be cannulated and formed of stainless steel, titanium, or Polyetheretherketone (i.e., PEEK) such that the devices may be biologically friendly, implantable into a human body without adverse effects and may retain desirable structural aspects. The components (e.g., male component 30, male component 330, male component 430, female component 20, female component 320, female component 420) of the bone fusion devices may also be cannulated as depicted and described or one or more of such components could be solid throughout or may include a combination of cannulated and solid portions. For example, a K-wire may be received in a cannula or cavity of a component(s) of a bone fusion device during a surgical procedure to align such a component(s).

Figure 13:
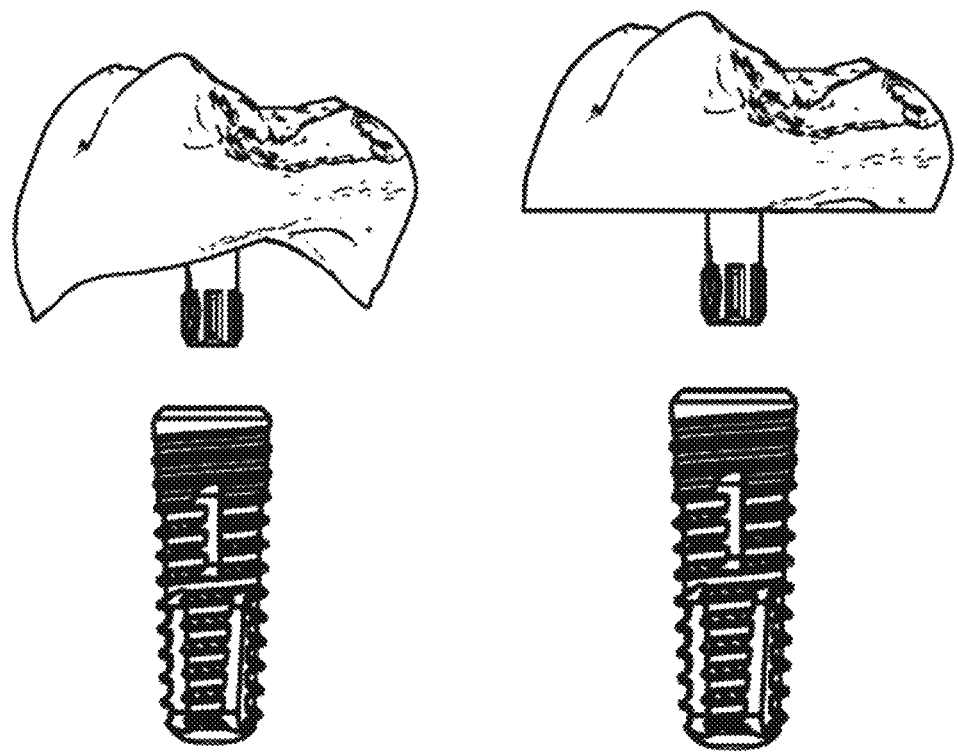
FIG. 13 is a side view of a male component connected to a dental post and a female component engageable with the male component.

As would be understood, the male and female components of the bone fusion devices (e.g., bone fusion device 10, bone fusion device 310, bone fusion device 410) described above, may be used to connect various bone portions to each other, such as bones of the joints of the foot described above. For example, a first component (e.g., male component 30, male component 330, male component 430) of such a bone fusion device may be screwed into a cavity by hand or via a driver (e.g., using a hex head driver received in a hexagonal shaped recess or on an outside surface of the first component) of a first bone, such as a proximal phalanx bone of the foot, while a second component (e.g., female component 20, female component 320, female component 420) may be screwed into a second bone, such as a middle phalanx bone of the foot, by hand or via a driver (e.g., using a hex head driver received in a hexagonal shaped recess or on an outside surface of the second component). The first and second components connected to the bones may be connected to each other as described above relative to the various components of the various bone fusion devices. As described above the above described bone fusion devices may be utilized to correct hammertoe deformities and similar deformities of the foot. Such devices may also be used for dental posts, surgical instrument connections, hip stem connections, knee platform connections, and other applications of joining bones while inhibiting rotation. Other applications include suture anchors, bone screws, bone plates. In an example, FIG. 13 depicts a dental post application including male component engaged with a tooth and female component engageable therewith and configured to engage with a jawbone of person or animal.

The terms circumference, circumferential and circumferentially as referred to herein refer to a circumference of a circular or cylindrical shaped object and refer to a perimeter of a cross-section of polygonally shaped objects (e.g., having a hexagonal or other polygonal cross-section) in a same way perpendicularly relative to an axis of such polygonally shaped objects.

The foregoing Detailed Description is understood as being in every respect illustrative and exemplary, but not restrictive, and the scope of the embodiments of the present disclosure disclosed herein is not to be determined from the Detailed Description, but rather from the claims as interpreted according to the full breadth permitted by the patent laws. It is understood that the embodiments shown and described herein are only illustrative of the principles of the present disclosure and that various modifications may be implemented by those skilled in the art without departing from the scope and spirit of the present disclosure. Those skilled in the art could implement various other feature combinations without departing from the scope and spirit of the present disclosure.

The invention claimed is:

1. A bone coupling device configured for joining a first bone piece to a second bone piece, the device comprising:
a first component comprising an inner surface bounding a first cavity and a first stem portion having external threads for insertion into the first bone piece;
a second component comprising a second stem portion having external threads for insertion into the second bone piece and an axially extending connector extending from the second stem portion and configured to be inserted into the first cavity;

said connector having an outer surface, said outer surface and said inner surface complementarily shaped to inhibit rotation relative to each other when said connector is received in said cavity to engage said first component and said second component;

each of said outer surface and said inner surface comprises a plurality of longitudinally extending substantially flat surfaces spaced circumferentially from each other about an axis of said first component and said second component, such that contact between said outer surface and said inner surface inhibits rotation of said first component and said second component relative to each other wherein inner flat surfaces of said plurality of longitudinally extending substantially flat surfaces forming said inner surface extend longitudinally along an entire length of said first cavity configured to receive said connector;

wherein two outer flat surfaces of said plurality of longitudinally extending substantially flat surfaces forming said outer surface bound an axially aligned slot extending through said outer surface and along a longitudinal portion of said two outer flat surfaces to allow elastic deformation of said connector;

wherein said outer surface comprises at least one locking projection having a larger radial dimension relative to a remainder of said outer surface, said at least one locking projection extending outwardly from at least one of said substantially flat surfaces of said outer surface, said at least one locking projection comprising an inclined surface configured to allow at least one of said inner flat surfaces of said first component to move along said inclined surface to said larger radial dimension of said at least one locking projection in response to an axial force engaging said first component and said second component to elastically deform said connector and provide a friction fit between said cavity of said first component and said connector of said second component to inhibit a separation of said connector from said cavity;

wherein said connector comprises a first end opposite said second stem portion toward said first component and a second end closest to said second stem portion, wherein said at least one locking projection is spaced longitudinally from said first end of said connector by a flat surface portion of said at least one of said substantially flat surfaces of said outer surface and said at least one locking projection is spaced longitudinally from said second end by a second flat surface portion of said at least one of said substantially flat surfaces of said outer surface.

2. The device of claim 1 wherein said slot connects a connector cavity in a radial interior of said connector with an exterior of said connector, said connector being deformable such that said two outer flat surfaces move closer to each other in response to said first component receiving said connector in said cavity and said at least one locking projection contacting said inner surface to provide the frictional fit.

3. The device of claim 2 wherein said at least one locking projection comprises a first locking projection and a second locking projection extending outwardly from said outer surface, said first locking projection and said second locking projection located opposite one another about said slot and bounding said slot.

4. The device of claim 2 wherein said at least one locking projection comprises a first locking projection and a second locking projection extending outwardly from said outer surface, said first locking projection and said second locking projection located on opposite longitudinal substantially flat surfaces bounding said slot.

5. The device of claim 2 wherein said at least one locking projection comprises a first locking projection and a second locking projection extending outwardly from said outer surface, said first locking projection and said second locking projection radially aligned with each other said axis of said first component and said second component.

6. The device of claim 4 wherein said first locking projection is located on a first portion of said connector and said second locking projection is located on a second portion of said connector, said slot extends through said connector from a lateral side to a second lateral side, said slot bounded by said first portion of said connector and said second portion of said connector, said connector elastically deformable such that said first portion and said second portion may deflect toward each other into said slot in response to a force being placed on at least one of said first locking portion or said second locking portion in response to the axial force engaging said first component and said second component to provide a friction fit between said first component and said second component.

7. The device of claim 1 wherein said outer surface of said connector and said inner surface of said first component are non-threaded.

8. The device of claim 1 wherein said longitudinal portion of said two outer flat surfaces extends less than an entire length of said outer surface.

9. The device of claim 1 wherein said inner surface forms a hexagonal cross-section along the entire length of said first cavity.

* * * * *